United States Patent
Mulder et al.

(10) Patent No.: US 11,504,405 B2
(45) Date of Patent: Nov. 22, 2022

(54) COMPOSITIONS COMPRISING BACTERIAL STRAINS

(71) Applicant: 4D Pharma Research Limited, Aberdeen (GB)

(72) Inventors: Imke Mulder, Aberdeen (GB); Alexander Stevenson, Aberdeen (GB); Helene Savignac, Aberdeen (GB)

(73) Assignee: 4D Pharma Research Limited, Aberdeen (GB)

( * ) Notice: Subject to any disclaimer, the term of this patent is extended or adjusted under 35 U.S.C. 154(b) by 0 days.

(21) Appl. No.: 17/149,990

(22) Filed: Jan. 15, 2021

(65) Prior Publication Data

US 2021/0275607 A1 Sep. 9, 2021

Related U.S. Application Data

(63) Continuation of application No. PCT/EP2019/069162, filed on Jul. 16, 2019.

(30) Foreign Application Priority Data

Jul. 16, 2018 (EP) ..................................... 18183619

(51) Int. Cl.
*A61K 35/741* (2015.01)
*A61P 11/00* (2006.01)

(52) U.S. Cl.
CPC ............ *A61K 35/741* (2013.01); *A61P 11/00* (2018.01)

(58) Field of Classification Search
None
See application file for complete search history.

(56) References Cited

U.S. PATENT DOCUMENTS

2016/0067188 A1  3/2016  Cade et al.

FOREIGN PATENT DOCUMENTS

| WO | WO-0185187 A1 | 11/2001 | |
|----|---------------|---------|---|
| WO | WO-03046580 A1 | 6/2003 | |
| WO | WO-2013008039 A2 | 1/2013 | |
| WO | WO-2013050792 A1 | 4/2013 | |
| WO | WO-2014167338 A1 | 10/2014 | |
| WO | WO-2016203218 A1 | 12/2016 | |
| WO | WO-2017148596 A1 | 9/2017 | |
| WO | WO-2018011593 A1 | 1/2018 | |
| WO | WO-2018011594 A1 | 1/2018 | |
| WO | WO-2018109461 A1 | 6/2018 | |
| WO | WO-2018187272 A1 * | 10/2018 | ............... A61P 1/00 |
| WO | WO-2019010255 A1 | 1/2019 | |

OTHER PUBLICATIONS

Bernalier et al. *Ruminococcus hydrogenotrophicus* sp. nov., a new H2/CO2-utilizing acetogenic bacterium isolated from human feces. 1996 Arch. Microbiol. 166 (3), 176-183. Sep. 1996.

Bernard, Gordon R. et al, Report of the American-European Consensus Conference on acute respiratory distress syndrome: Definitions, mechanisms, relevant outcomes, and clinical trial coordination, Journal of Critical Care, vol. 9, Issue 1,1994,pp. 72-81, ISSN 0883-9441,https://doi.org/10.1016/0883-9441(94)90033-7.

Dayhoff et al, A Model of Evolutionary Change in Proteins,1978, Atlas of Protein Sequence and Structure, vol. 5, supp 3.

Eckburg, PB. et al., Diversity of the human intestinal microbial flora.Science. Jun. 10, 2005;308(5728):1635-8. Epub Apr. 14, 2005.

Frank, D. et al., Molecular-phylogenetic characterization of microbial community imbalances in human inflammatory bowel diseases. 2007. PNAS. 104(34):13780-5.online Aug. 15, 2007.

Hudson LD, Steinberg KP., Epidemiology of acute lung injury and ARDS, Chest. Jul. 1999;116(1 Suppl):74S-82S. doi: 10.1378/chest.116.suppl_1.74s-a.PMID: 10424602.

International Search Report dated Oct. 31, 2019 for International Application Serial No. PCT/EP2019/069162,(4 pages).

Kang, S. et al. (2010) "Dysbiosis of fecal microbiota in Crohn's disease patients as revealed by a custom phylogenetic microarray," Inflammatory Bowel Diseases. Dec. 2010;16(12):2034-2042.doi: 10.1002/ibd.21319.

Lee, et al. Intestinal microbiota in pathophysiology and management of irritable bowel syndrome . 2014. World J Gastroenterol. 20(27): 8886-8897.

Leslie, et al., Trehalose and sucrose protect both membranes and proteins in intact bacteria during drying. (1995) Appl. Environ. Microbiol. 61, 3592-3597.

Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.

Lopetuso, Loris et al., Commensal Clostridia: Leading players in the maintenance of gut homeostasis, Gut Pathogens, 5(1):23, DOI: 10.1186/1757-4749-5-23.

Machiels, K., A decrease of the butyrate-producing species *Roseburia hominis* and *Faecalibacterium prausnitzii* defines dysbiosis in patients with ulcerative colitis. Gut. Aug. 2014;63(8):1275-83. doi: 10.1136/gutjnl-2013-304833. Epub Sep. 10, 2013.

Macpherson, AJ. et al., IgA responses in the intestinal mucosa against pathogenic and non-pathogenic microorganisms. Oct. 2001. 3(12). 1021-1035.

Macpherson, AJ., et al., The functions of mucosal T cells in containing the indigenous commensal flora of the intestine.Cell Mol Life Sci. Dec. 2002;59(12):2088-96.

(Continued)

*Primary Examiner* — Brian Gangle
(74) *Attorney, Agent, or Firm* — Wilson Sonsini Goodrich & Rosati

(57) ABSTRACT

The invention provides compositions comprising bacterial strains for treating and preventing lung injury or lung disease.

20 Claims, 4 Drawing Sheets

Specification includes a Sequence Listing.

(56) References Cited

OTHER PUBLICATIONS

Martin et al., Cloning, Nucleotide Sequence, and Taxonomic Implications of the Flagellin Gene of Roseburia cecicola, Journal of Bacteriology. Jun. 1988; 170(6):2612-2617.
Masco, L., et al., Identification of *Bifidobacterium* Species Using rep-PCR Fingerprinting. Systematic and Applied Microbiology 26(4):557-63 ∎ Nov. 2003.
Mazmanian, SK., An immunomodulatory molecule of symbiotic bacteria directs maturation of the host immune system. Cell. Jul. 15, 2005;122(1):107-18.
Mitropoulou, G. et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Pierrakos, Charalampos et al., Acute respiratory distress syndrome: pathophysiology and therapeutic options, Journal of clinical medicine research vol. 4,1 (2012): 7-16.doi:10.4021/jocmr761w.
Rubenfeld GD, et al., Incidence and outcomes of acute lung injury, N Engl J Med. Oct. 20, 2005;353(16):1685-93. doi: 10.1056/NEJMoa050333. PMID:16236739.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Smith and Waterman, "Comparison of biosequences", Advances in Applied Mathematics, vol. 2, Issue 4, Dec. 1981, pp. 482-489.
Smith et al. Comparison of Biosequences. Advances in Applied Mathematics. 2:482-489 (1981).
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Strobel, H.J. Basic laboratory culture methods for anaerobic bacteria. Methods Mol Biol. 2009;581:247-61. doi: 10.1007/978-1-60761-214-8_16.
Su,X., Wang, L., Song, Y. et al., Inhibition of inflammatory responses by ambroxol, a mucolytic agent, in a murine model of acute lung injury induced by lipopolysaccharide, Intensive Care Med 30, 133-140 (2004).https://doi.org/10.1007/s00134-003-2001-y.
Tap et al. Towards the human intestinal microbiota phylogenetic core. 2009. Environ Microbiol, 11(10):2574-84.EpubJul. 6, 2009.
Ware LB, Matthay MA, The acute respiratory distress syndrome, N Engl J Med. May 4, 2000;342(18):1334-49. doi:10.1056/NEJM200005043421806. PMID: 10793167.
Written Opinion of the International Searching Authority dated Oct. 31, 2019 for International Application Serial No. PCT/EP2019/069162, (5 pages).
Kailasapathy, K. Microencapsulation of Probiotic Bacteria:Technology and Potential Applications. Curr. Issues Intest. Microbiol. (2002) 3: 39-48.

* cited by examiner

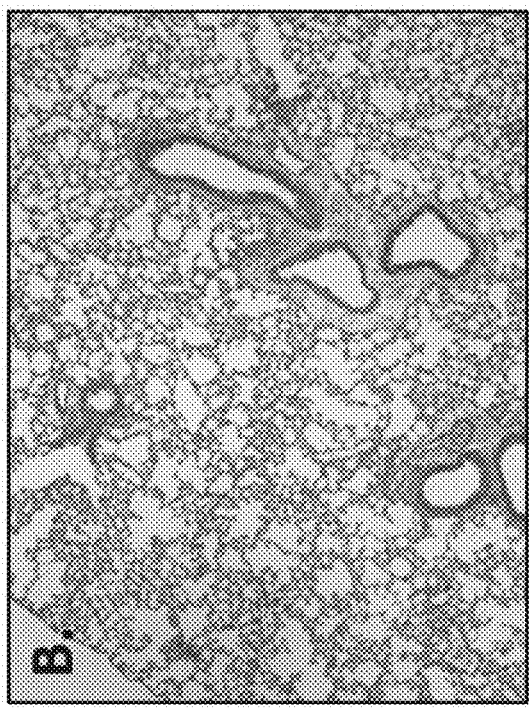
FIG. 3A
FIG. 3B
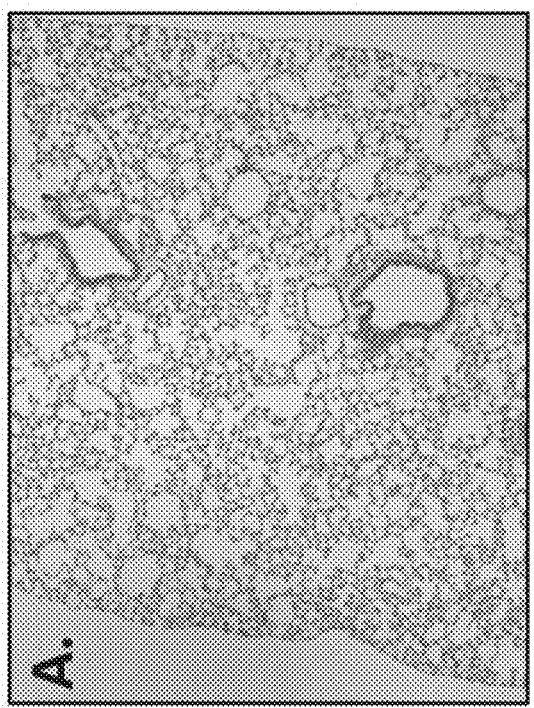
FIG. 3C
FIG. 3D

SEQUENCE LISTING

<160> NUMBER OF SEQ ID NOS: 1

<210> SEQ ID NO 1
<211> LENGTH: 1458
<212> TYPE: DNA
<213> ORGANISM: Blautia hydrogenotrophica strain S5a36
<220> FEATURE:
<221> NAME/KEY: misc_feature
<222> LOCATION: 1416
<223> OTHER INFORMATION: n is any one of a, t, c or g

```
<400> SEQUENCE: 1
gatgaacgct ggcggcgtgc ttaacacatg caagtcgaac gaagcgatag agaacggaga      60
tttcggttga agttttctat tgactgagtg gcggacgggt gagtaacgcg tgggtaacct     120
gccctataca gggggataac agttagaaat gactgctaat accgcataag cgcacagctt     180
cgcatgaagc ggtgtgaaaa actgaggtgg tataggatgg acccgcgttg gattagctag     240
ttggtgaggt aacggcccac caaggcgacg atccatagcc ggcctgagag ggtgaacggc     300
cacattggga ctgagacacg gcccaaactc ctacgggagg cagcagtggg gaatattgca     360
caatggggga aaccctgatg cagcgacgcc gcgtgaagga agaagtatct cggtatgtaa     420
acttctatca gcagggaaga aagtgacggt acctgactaa gaagcccgg ctaattacgt      480 gccagcagcc gcggtaatac gtaaggggca agcgttatcc ggatttactg ggtgtaaagg     540
gagcgtagac ggtttggcaa gtctgatgtg aaaggcatgg gctcaacctg tggactgcat     600
tggaaactgt cagacttgag tgccggagag gcaagcggaa ttcctagtgt agcggtgaaa     660
tgcgtagata ttaggaggaa caccagtggc gaaggcggcc tgctggacgg taactgacgt     720
tgaggctcga aagcgtgggg agcaaacagg attagatacc ctggtagtcc acgctgtaaa     780
cgatgaatac taggtgtcgg gtggcaaagc cattcggtgc cgcagcaaac gcaataagta     840
ttcccacctg gggagtacgt tcgcaagaat gaaactcaaa ggaattgacg gggacccgca     900
caagcggtgg agcatgtggt ttaattcgaa gcaacgcgaa gaaccttacc aaatcttgac     960
atccctctga ccgggaagta atgttccctt ttcttcggaa cagaggagac aggtggtgca    1020
tggttgtcgt cagctcgtgt cgtgagatgt tgggttaagt cccgcaacga gcgcaaccct    1080
tattcttagt agccagcagg tagagctggg cactctaggg agactgccag ggataacctg    1140
gaggaaggtg gggatgacgt caaatcatca tgccccttat gatttgggct acacacgtgc    1200
tacaatggcg taaacaaagg gaagcgaagg ggtgacctgg agcaaatctc aaaaataacg    1260
tctcagttcg gattgtagtc tgcaactcga ctacatgaag ctggaatcgc tagtaatcgc    1320
gaatcagaat gtcgcggtga atacgttccc gggtcttgta cacaccgccc gtcacaccat    1380
gggagtcagt aacgcccgaa gtcagtgacc caaccnaaag gagggagctg ccgaaggtgg    1440
gactgataac tggggtga                                                 1458
```

COMPOSITIONS COMPRISING BACTERIAL STRAINS

CROSS-REFERENCE

This application is a continuation of International Application No. PCT/EP2019/069162, filed Jul. 16, 2019, which claims the benefit of European Application No. 18183619.8, filed Jul. 16, 2018, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 14, 2021, is named 56708_745_301_sequence_listing.txt and is 4,096 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 1500 different phylotypes, dominated in abundance levels by two major bacterial divisions (*Phyla*), the Bacteroidetes and the Firmicutes [2-3]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host and additional health benefits. Similarly, the immunological importance of the gut microbiota is well-recognized and is exemplified in germfree animals which have an impaired immune system that is functionally reconstituted following the introduction of commensal bacteria [4-6].

Dramatic changes in microbiota composition have been documented in gastrointestinal disorders such as inflammatory bowel disease (IBD). For example, the levels of *Clostridium* cluster XIVa bacteria and *Clostridium* cluster XI (*F. prausnitzii*) are reduced in IBD patients whilst numbers of *E. coli* are increased, suggesting a shift in the balance of symbionts and pathobionts within the gut [7-11].

In recognition of the potential positive effect that certain bacterial strains may have on the animal gut and other tissues, various strains have been proposed for use in the treatment of various diseases (see, for example, [12-15]). A number of strains, including mostly *Lactobacillus* and *Bifidobacterium* strains, have been proposed for use in treating various bowel disorders (see [16] for a review). Strains of the species *Blautia hydrogenotrophica* have also been proposed for use in treating bowel disorders [17-19]. Strains of the genus *Blautia* have also been proposed for use in modulating the microbial balance of the digestive ecosystem [20] and particular species have been proposed for use in treating systemic diseases distanced from the gut [21]. However, the relationship between different bacterial strains and different diseases, and the precise effects of particular bacterial strains on the gut and other tissues at a systemic level, and on any particular types of diseases, are poorly characterised.

There is a requirement for the potential effects of gut bacteria to be characterised so that new therapies using gut bacteria can be developed.

SUMMARY OF THE INVENTION

The inventors have developed new therapies for treating lung injury or lung disease. In particular, the inventors have identified that strains of the species *Blautia hydrogenotrophica* can be effective for treating lung injury or lung disease. As described in the examples, administration of compositions comprising strains of the species *Blautia hydrogenotrophica* reduce inflammation of the lung tissue in a lipopolysaccharide (LPS)-induced mouse model of lung injury. Therefore, compositions comprising strains of the species *Blautia hydrogenotrophica* may treat lung injury or lung disease.

In a first aspect, the invention provides a composition comprising a bacterial strain of the species *Blautia hydrogenotrophica*, for use in a method of treating lung injury or lung disease. The invention also provides a method of treating lung injury or lung disease, comprising administering a composition comprising a bacterial strain of the species *Blautia hydrogenotrophica* to a patient in need thereof. Furthermore, the invention provides a use of a composition comprising a bacterial strain of the species *Blautia hydrogenotrophica* for the manufacture of a medicament for the treatment of lung injury or lung disease.

In a preferred embodiment, the invention provides a composition comprising a bacterial strain of the species *Blautia hydrogenotrophica*, for use in a method of treating lung injury or lung disease, wherein the lung injury or lung disease is mediated by inflammation. In a preferred embodiment, the invention provides a composition comprising a bacterial strain of the species *Blautia hydrogenotrophica*, for use in a method of treating lung injury or lung disease, wherein the composition reduces inflammation of the lung tissue. In a preferred embodiment, the invention provides a composition comprising a bacterial strain of the species *Blautia hydrogenotrophica*, for use in a method of treating asthma. In a preferred embodiment, the invention provides a composition comprising a bacterial strain of the species *Blautia hydrogenotrophica*, for use in a method of treating acute respiratory distress syndrome (ARDS). In a preferred embodiment, the invention provides a composition comprising a bacterial strain of the species *Blautia hydrogenotrophica*, for use in a method of treating chronic obstructive pulmonary disease (COPD).

The bacterial strain of the species *Blautia hydrogenotrophica* may have a 16s rRNA gene sequence that is at least 95%, 96%, 97%, 98%, 99%, 99.5% or 99.9% identical to the 16s rRNA gene sequence of a bacterial strain of *Blautia hydrogenotrophica*. Strains which are closely related to a bacterial strain of the species *Blautia hydrogenotrophica* may also be used in the invention, such as bacterial strains that have a 16s rRNA gene sequence that is at least 95%, 96%, 97%, 98%, 99%, 99.5% or 99.9% identical to SEQ ID NO:1. In other embodiments, the bacterial strain in the composition has a 16s rRNA gene sequence that is at least 95%, 96%, 97%, 98%, 99%, 99.5% or 99.9% identical to SEQ ID NO: 1. Preferably, the bacterial strain for use in the invention has the 16s rRNA gene sequence represented by SEQ ID NO:1. Most preferably, the bacterial strain in the composition for use in the invention is the *Blautia hydrogenotrophica* strain deposited under accession number DSM 14294. Derivatives of the *Blautia hydrogenotrophica* strain deposited under accession number DSM 14294 may also be used.

In certain embodiments, the composition of the invention is for oral administration. Oral administration of the strains of the invention can be effective for treating lung injury or lung disease. Also, oral administration is convenient for patients and practitioners and allows delivery to and/or partial or total colonisation of the intestine.

In certain embodiments, the composition of the invention comprises one or more pharmaceutically acceptable excipients or carriers.

In certain embodiments, the composition of the invention comprises a bacterial strain that has been lyophilised. The composition of the invention can also comprise a lyophilised bacteria strain of the species *Blautia hydrogenotrophica*. Lyophilisation is an effective and convenient technique for preparing stable compositions that allow delivery of bacteria.

In certain embodiments, the invention provides a food product comprising the composition as described above.

In certain embodiments, the invention provides a vaccine composition comprising a bacterial strain as described above.

Additionally, the invention provides a method of treating lung injury or lung disease, comprising administering a composition comprising a bacterial strain of *Blautia hydrogenotrophica* to a patient in need thereof.

BRIEF DESCRIPTION OF DRAWINGS

FIGS. 3A-3H: Lung histopathology representative images. FIG. 3A: Mouse 1.1, ×10; normal lung (total score of 0); FIG. 3B: Mouse 4.3, ×10 (total score of 3); inflammatory aggregates with peribronchiolar, perivascular and intra-alveolar distribution; FIG. 3C: Mouse 5.8, ×10 (total score of 2); inflammatory changes as above for 4.3; FIGS. 3D and 3E: Mouse 6.6, ×10 and ×40 (total score of 5); peribronchiolar, perivascular and intra-alveolar inflammation; high power shows a degenerate arterial vessel with fibrinoid necrosis of the wall and infiltrating granulocytes adjacent to a zone of intense intra-alveolar inflammation; FIG. 3F: Mouse 6.10, ×10 (total score of 5); extensive intra-alveolar haemorrhage, but with minimal inflammatory change; FIG. 3G: Mouse 7.10, ×10 (total score of 3); multifocal inflammatory change; FIG. 3H: Mouse 8.8, ×10 (total score of 2); multifocal inflammatory change.

DISCLOSURE OF THE INVENTION

Bacterial Strains

Figure 1:
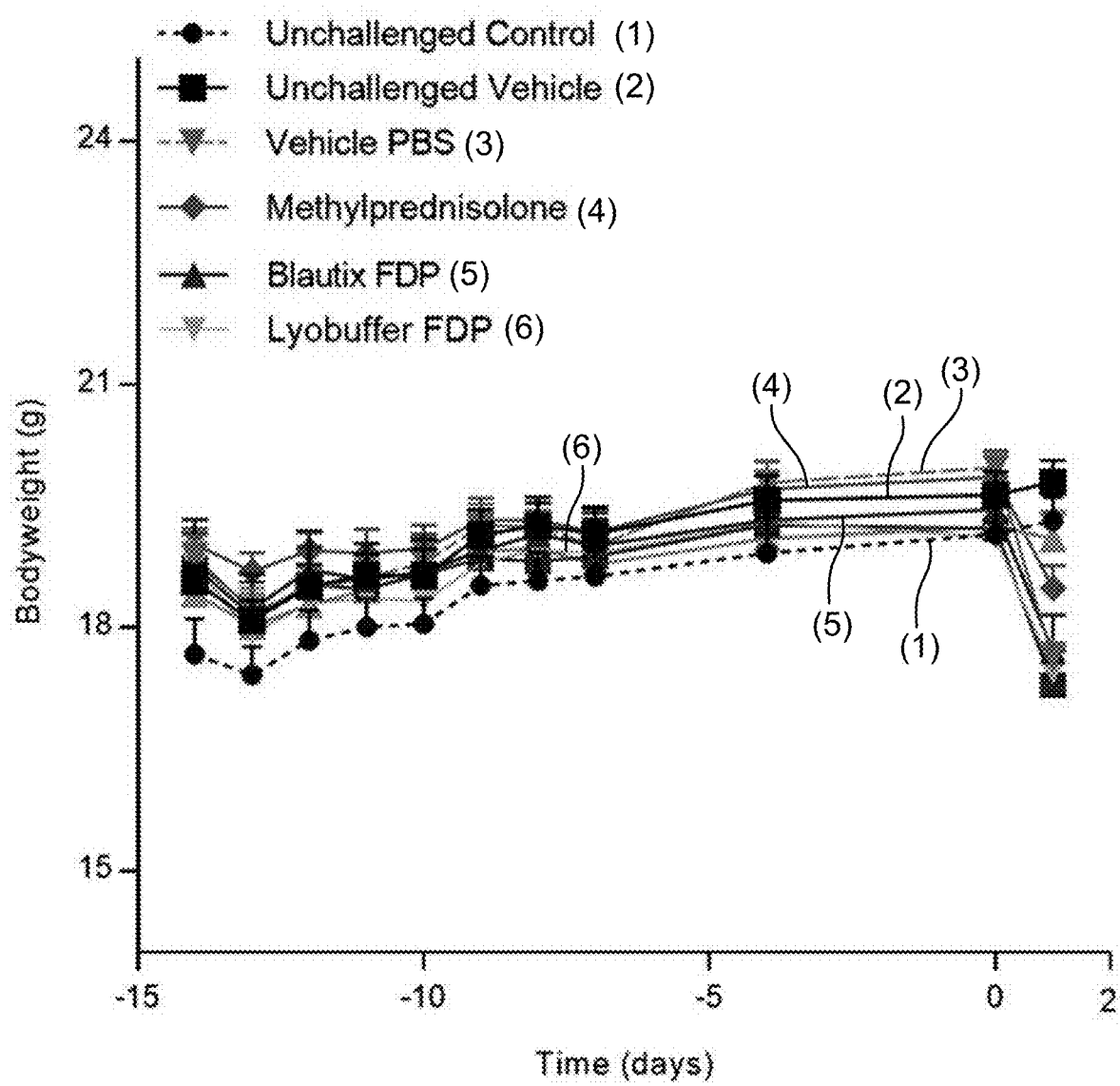
FIG. 1: Groups 1-6 bodyweights; data are presented as mean±SEM.

The compositions of the invention comprise a bacterial strain of the species *Blautia hydrogenotrophica*. The examples demonstrate that such a bacterial strain is useful for treating lung injury or lung disease, in particular lung injuries or lung diseases mediated by inflammation.

The genus *Blautia* are Gram-reaction-positive, non-motile bacteria that may be either coccoid or oval and all are obligate anaerobes that produce acetic acid as the major end product of glucose fermentation [22].

*Blautia hydrogenotrophica* (previously known as *Ruminococcus hydrogenotrophicus*) has been isolated from the guts of mammals, is a strictly anaerobic, non-sporulating cocobacilli, and metabolises $H_2/CO_2$ to acetate, which may be important for human nutrition. The type strain of *Blautia hydrogenotrophica* is S5a33=JCM 14656. The GenBank accession number for the 16S rRNA gene sequence of *Blautia hydrogenotrophica* strain S5a36 is X95624.1 (disclosed herein as SEQ ID NO:1). This exemplary *Blautia hydrogenotrophica* strain is described in [22] and [23]. The S5a33 strain and the S5a36 strain correspond to two sub-clones of a strain isolated from a faecal sample of a healthy subject. They show identical morphology, physiology and metabolism and have identical 16S rRNA gene sequences. Thus, in some embodiments, the *Blautia hydrogenotrophica* for use in the invention has the 16S rRNA gene sequence of SEQ ID NO:1.

The *Blautia hydrogenotrophica* bacterium deposited under accession number DSM 14294 was tested in the examples and is also referred to herein as strain BH and Blautix. Strain BH is the preferred strain of the invention. Strain BH was deposited with the Deutsche Sammlung von Mikroorganismen [German Microorganism Collection] (Mascheroder Weg 1b, 38124 Braunschweig, Germany) as "*Ruminococcus hydrogenotrophicus*" under accession number DSM 14294 as "S5a33" on 10 May 2001. The depositor was INRA Laboratoire de Microbiologie C R de Clermont-Ferrand/Theix 63122 Saint Genès Champanelle, France. Ownership of the deposit has passed to 4D Pharma Plc by way of assignment. 4D Pharma Plc has authorised, by way of an agreement, 4D Pharma Research Limited to refer to the deposited biological material in the application and has given its unreserved and irrevocable consent to the deposited material being made available to the public. The DSM 14294 deposit is referenced in [20].

Bacterial strains closely related to the strain tested in the examples are also expected to be effective for treating lung injury or lung disease, in particular lung injury or lung diseases mediated by inflammation. In certain embodiments, the bacterial strain for use in the invention has a 16s rRNA gene sequence that is at least 95%, 96%, 97%, 98%, 99%, 99.5% or 99.9% identical to SEQ ID NO:1. Preferably, the bacterial strain has the 16s rRNA gene sequence represented by SEQ ID NO:1. Most preferably, the bacterial strain is the *Blautia hydrogenotrophica* strain deposited under accession number DSM 14294.

In certain embodiments, a composition of the invention comprises a biotype of the bacterium deposited under accession number DSM 14294. A biotype of the strain deposited under accession number DSM 14294 is a closely related strain that has the same or very similar physiological and biochemical characteristics. A biotype will have comparable immune modulatory activity to the original DSM 14294. A biotype will therefore be effective in treating lung injury or lung disease, in particular lung injuries or lung diseases mediated by inflammation, including asthma, ARDS or COPD.

A biotype will elicit comparable effects on lung injury or lung disease to the effects shown in the examples, which may be identified by using the culturing and administration protocols described in the examples. In particular, a biotype will elicit a reduction of lung inflammation comparable to that of a bacterium deposited under accession number DSM 14294.

Strains that are biotypes of a bacterium deposited under accession number DSM 14294 and that are suitable for use in the invention may be identified by sequencing other nucleotide sequences for a bacterium deposited under accession number DSM 14294. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, $(GTG)_5$, or REP [24]. Biotype strains may have such sequences with at least 95%, 96%, 97%, 98%, 99%, 99.5% or 99.9% sequence identity to the corresponding sequence of a bacterium deposited under accession number DSM 14294. In some embodiments, a biotype strain may have a 16S rRNA gene sequence with at least 95%, 96%, 97%, 98%, 99%, 99.5% or 99.9% sequence identity to the 16S rRNA gene sequence of SEQ ID NO:1.

Alternatively, strains that are biotypes of a bacterium deposited under accession number DSM 14294 and that are suitable for use in the invention may be identified by using the accession number DSM 14294 deposit, and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other *Blautia hydrogenotrophica* strains.

In certain embodiments, strains that are biotypes of a bacterium deposited under accession number DSM 14294 and that are suitable for use in the invention are strains that provide the same pattern as a bacterium deposited under accession number DSM 14294 when analysed by amplified ribosomal DNA restriction analysis (ARDRA), for example when using Sau3AI restriction enzyme (for exemplary methods and guidance see, for example [25]). Alternatively, biotype strains are identified as strains that have the same carbohydrate fermentation patterns as a bacterium deposited under accession number DSM 14294.

In some embodiments, the bacterial strain used in the invention is:
(i) Positive for one or both of α-glucosidase and alkaline phosphatase; and/or
(ii) Negative for at least one of (e.g. at least 2, 3, 4, 5, 6, 7, 8, 9, 10, 11, 12, 13, 14, 15, 16, 17, 18, 19, 20, 21, 22, 23, 24, 25, 26 or all of): urease, arginine dihydrolase, α-galactosidase, β-galactosidase, β-galactosidase 6 phosphate, β-glucosidase, α-arabinosidase, β-glucuronidase, N-acetyl-β-glucosaminidase, mannose fermentation, raffinose fermentation, glutamic acid decarboxylase, α-fucosidase, reduction of nitrates, indole production, arginine arylamidase, proline arylamidase, leucyl glycine arylamidase, phenylalanine arylamidase, leucine arylamidase, pyroglutamic acid arylamidase, tyrosine arylamidase, alanine arylamidase, glycine arylamidase, histidine arylamidase, glutamyl glutamic acid arylamidase and serine arylamidase;
preferably as determined by an assay of carbohydrate, amino acid and nitrate metabolism, and optionally an assay of alkaline phosphatase activity, more preferably as determined by Rapid ID 32A analysis (preferably using the Rapid ID 32A system from bioMérieux).

Other *Blautia hydrogenotrophica* strains that are useful in the compositions and methods of the invention, such as biotypes of a bacterium deposited under accession number DSM 14294, may be identified using any appropriate method or strategy, including the assays described in the examples. In particular, bacterial strains that have similar growth patterns, metabolic type and/or surface antigens to a bacterium deposited under accession number DSM 14294 may be useful in the invention. A useful strain will have comparable microbiota modulatory activity to the DSM 14294 strain. In particular, a biotype strain will elicit comparable effects on lung injury or lung disease to the effects shown in the examples, which may be identified by using the culturing and administration protocols described in the examples.

A particularly preferred strain of the invention is the *Blautia hydrogenotrophica* strain deposited under accession number DSM 14294. This is the exemplary BH strain tested in the examples and shown to be effective for treating lung injury or lung disease. Therefore, the invention provides a cell, such as an isolated cell, of the *Blautia hydrogenotrophica* strain deposited under accession number DSM 14294, or a derivative thereof, for use in therapy, in particular for the injuries and diseases described herein.

In certain embodiments, a composition of the invention comprises a derivative of the bacterium deposited under accession number DSM 14294. A derivative of the strain deposited under accession number DSM 14294 may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable immune modulatory activity to the original DSM 14294 strain. A derivative strain will have comparable microbiota modulatory activity to the original DSM 14294 strain. A derivative strain will therefore be effective in treating lung injury or lung disease, in particular lung injuries or lung diseases mediated by inflammation, including asthma, ARDS or COPD.

A derivative strain will elicit comparable effects on lung injury or lung disease to the effects shown in the examples, which may be identified by using the culturing and administration protocols described in the examples. In particular, a derivative strain will elicit an effect on lung inflammation comparable to that of a bacterium deposited under accession number DSM 14294. A derivative of the DSM 14294 strain will generally be a biotype of the DSM 14294 strain.

The bacterial strain may also be a strain that has the same safety and therapeutic efficacy characteristics as the strain deposited under accession number DSM 14294, and such cells are encompassed by the invention. The composition can therefore comprise a *Blautia hydrogenotrophica* strain that is not the strain deposited under accession number DSM 14294 but has the same safety and therapeutic efficacy characteristics as the strain deposited under accession number DSM 14294. The safety characteristics of a strain can be established for example by testing the resistance of the strain to antibiotics, for example distinguishing between intrinsic and transmissible resistance to antibiotics. The safety characteristics of a strain can also be established by evaluating the pathogenic properties of a strain in vitro, for example the levels of toxin production. Other safety tests include testing the acute or chronic toxicity of the bacterial strain in rat and mice models. The therapeutic efficacy of a strain can be established by functional characterization of the bacterial strain in vitro and in vivo using a relevant model.

In preferred embodiments, the bacterial strains in the compositions of the invention are viable and capable of partially or totally colonising the intestine. Preferably, the compositions disclosed herein are to be administered to the gastrointestinal tract in order to enable delivery to and/or partial or total colonisation of the intestine with the bacterial strain of the invention. In other words, the bacteria may have colonised some or all of the gastrointestinal tract and/or such colonisation may be transient or permanent.

More specifically, in some embodiments, the "total colonisation of the intestine" means that bacteria have colonised all parts of the intestine (i.e. the small intestine, large intestine and rectum). Additionally or alternatively, the term "total colonisation" means that the bacteria engraft permanently in the some or all parts of the intestine.

In some embodiments, "partial colonisation of the intestine" means that bacteria have colonised some but not all parts of the intestine. Additionally or alternatively, the term "partial colonisation" means that the bacteria engraft transiently in some or all parts of the intestine.

The transience of engraftment can be determined by assessing (e.g. in a fecal sample) the abundance of the bacterial strain of the invention periodically (e.g. daily) following the end of a dosing interval to determine the washout period, i.e. the period between conclusion of the dosing interval and there being no detectable levels of the bacterial strain of the invention present. In embodiments of the invention, the washout period is 14 days or less, 12 days or less, 10 days or less, 7 days or less, 4 days or less, 3 days or less, 2 days or less or 1 day or less.

In embodiments of the invention, the bacteria of the present invention engraft transiently in the large intestine.

Therapeutic Uses

Lung Injury or Lung Disease

The bacterial compositions of the invention are for use in treating lung disease or lung injury. The bacterial compositions of the invention are also for use in preventing lung disease or lung injury.

As demonstrated in the examples, the bacterial compositions of the invention are effective in reducing inflammation in the tissue of the lungs. Treatment with compositions of the invention results in a reduction in signs of lung inflammation as measured by a qualified histopathologist. Therefore, the compositions of the invention may be useful for treating lung injury or lung disease, in particular lung injuries or lung diseases mediated by inflammation. In particular, the compositions of the invention may be useful for treating lung injury or lung disease by reducing inflammation in the tissue of the lungs. In particular, the compositions of the invention may be useful for treating lung injury or lung disease by reducing damage caused by lung injury or lung disease.

Lung injury and lung disease encompass all pathological conditions affecting the organs and tissues that make gas exchange possible in higher organisms. Lung injury and lung disease can affect, for example, one or more of the upper respiratory tract, lower respiratory tract, trachea, bronchi, bronchioles, alveoli, interstitium, pleura, pleural cavity, and the nerves and muscles of breathing.

In some embodiments the compositions of the invention are for use in treating lung injury or lung disease which affects the upper respiratory tract. In some embodiments the compositions of the invention are for use in treating lung injury or lung disease which affects the lower respiratory tract. In some embodiments the compositions of the invention are for use in treating lung injury or lung disease which affects the trachea. In some embodiments the compositions of the invention are for use in treating lung injury or lung disease which affects the bronchi. In some embodiments the compositions of the invention are for use in treating lung injury or lung disease which affects the bronchioles. In some embodiments the compositions of the invention are for use in treating lung injury or lung disease which affects the alveoli. In some embodiments the compositions of the invention are for use in treating lung injury or lung disease which affects the interstitium. In some embodiments the compositions of the invention are for use in treating lung injury or lung disease which affects the pleura. In some embodiments the compositions of the invention are for use in treating lung injury or lung disease which affects the pleural cavity. In some embodiments the compositions of the invention are for use in treating lung injury or lung disease which affects the nerves and muscles of breathing. Preferably, the compositions of the invention are for use in treating lung injury or lung disease which is not asthma.

In some embodiments, the compositions of the invention are for use in treating ARDS, asthma, bronchiectasis, bronchiolitis, bronchitis, chronic cough, COPD, cystic fibrosis, emphysema, human metapneumovirus (hMPV) infection, influenza, pandemic flu, pertussis, pleurisy, pleural cavity diseases, pneumonia, respiratory syncytial virus (RSV), sarcoidosis, severe acute respiratory syndrome (SARS), tuberculosis or upper respiratory tract infections (such as the common cold, sinusitis, tonsillitis, pharyngitis and laryngitis).

In some embodiments the compositions of the invention are for use in treating ARDS. In some embodiments the compositions of the invention are for use in treating asthma. In some embodiments the compositions of the invention are for use in treating bronchiectasis. In some embodiments the compositions of the invention are for use in treating bronchiolitis. In some embodiments the compositions of the invention are for use in treating bronchitis. In some embodiments the compositions of the invention are for use in treating chronic cough. In some embodiments the compositions of the invention are for use in treating COPD. In some embodiments the compositions of the invention are for use in treating cystic fibrosis. In some embodiments the compositions of the invention are for use in treating emphysema. In some embodiments the compositions of the invention are for use in treating hMPV. In some embodiments the compositions of the invention are for use in treating influenza. In some embodiments the compositions of the invention are for use in treating pandemic flu. In some embodiments the compositions of the invention are for use in treating pertussis. In some embodiments the compositions of the invention are for use in treating pleurisy. In some embodiments the compositions of the invention are for use in treating pleural cavity diseases. In some embodiments the compositions of the invention are for use in treating pneumonia. In some embodiments the compositions of the invention are for use in treating RSV. In some embodiments the compositions of the invention are for use in treating sarcoidosis. In some embodiments the compositions of the invention are for use in treating SARS. In some embodiments the compositions of the invention are for use in treating tuberculosis. In some embodiments the compositions of the invention are for use in treating upper respiratory tract infections such as the common cold, sinusitis, tonsillitis, pharyngitis or laryngitis.

In some embodiments the compositions of the invention are for use in reducing damage caused by ARDS. In some embodiments the compositions of the invention are for use in reducing damage caused by asthma. In some embodiments the compositions of the invention are for use in reducing damage that is not caused by asthma. In some embodiments the compositions of the invention are for use in reducing damage caused by bronchiectasis. In some embodiments the compositions of the invention are for use in reducing damage caused by bronchiolitis. In some embodiments the compositions of the invention are for use in reducing damage caused by bronchitis. In some embodiments the compositions of the invention are for use in reducing damage caused by chronic cough. In some embodiments the compositions of the invention are for use in reducing damage caused by COPD. In some embodiments the compositions of the invention are for use in reducing damage caused by cystic fibrosis. In some embodiments the compositions of the invention are for use in reducing damage caused by emphysema. In some embodiments the compositions of the invention are for use in reducing damage caused by hMPV. In some embodiments the compositions of the invention are for use in reducing damage caused by influenza. In some embodiments the compositions of the invention are for use in reducing damage caused by pandemic flu. In some embodiments the compositions of the invention are for use in reducing damage caused by pertussis. In some embodiments the compositions of the invention are for use in reducing damage caused by pleurisy. In some embodiments the compositions of the invention are for use in reducing damage caused by pleural cavity diseases. In some embodiments the compositions of the invention are for use in reducing damage caused by pneumonia. In some embodiments the compositions of the invention are for use in reducing damage caused by RSV. In some embodiments the compositions of the invention are for use in reducing damage caused by sarcoidosis. In some embodiments the compositions of the invention are for use in reducing damage caused by SARS. In some embodiments the compositions of the invention are for use in reducing damage caused by tuberculosis. In some embodiments the compositions of the invention are for use in reducing damage caused by upper respiratory tract infections such as the common cold, sinusitis, tonsillitis, pharyngitis or laryngitis.

The examples show that treatment with a composition of the invention results in a reduction in the signs of lung inflammation as measured by a qualified histopathologist. In some embodiments, the compositions of the invention treat lung injury or lung disease by reducing neutrophil inflammation. In some embodiments, the compositions of the invention treat lung injury or lung disease by reducing haemorrhage. In some embodiments, the compositions of the invention treat lung injury or lung disease by reducing oedema. In some embodiments, the compositions of the invention treat lung injury or lung disease by reducing necrosis. In some embodiments, the compositions of the invention treat lung injury or lung disease by reducing atelectasis.

Asthma

The bacterial compositions of the invention are for use in treating asthma. The bacterial compositions of the invention are also for use in preventing asthma.

In preferred embodiments, the compositions of the invention are for use in treating asthma. In preferred embodiments, the compositions of the invention comprise a strain of the species *Blautia hydrogenotrophica* and are for use in treating asthma.

As demonstrated in the examples, treatment with compositions of the invention results in a reduction in signs of lung inflammation as measured by a qualified histopathologist, so compositions of the invention may be useful in the treatment of asthma.

Asthma is a disease characterised by chronic inflammation and restriction of the airways. Most commonly, asthma is characterised by chronic inflammation of the bronchi and bronchioles, resulting in narrowing of the same. Symptoms of asthma include wheezing, coughing, chest tightness, and/or shortness of breath. Symptoms can be more severe at certain times, for example at night, in the early morning, or after exercise.

Asthma is primarily classified by severity and frequency of symptoms. For example, asthma can be classified as intermittent asthma, mild persistent asthma, moderate persistent asthma or severe persistent asthma. Asthma can also be classified more simply as mild, moderate or severe. Asthma can also be classified as either being triggered by allergens that produce a cascade of inflammatory events mediated by T helper type 2 lymphocyte (Th2) processes, known as Th2-high asthma, or as being triggered by processes that are not Th2-mediated, known as non-Th2 asthma or Th2-low asthma. Non-Th2 or Th2-low asthma does not typically respond to inhaled corticosteroid therapy. Asthma can also be classified as allergic (also called atopic or extrinsic) or non-allergic (also called non-atopic or intrinsic), based on whether symptoms are precipitated by allergens or not. Allergic asthma is a form of Th2-high asthma. Non-allergic asthma is a form of non-Th2 or Th2-low asthma.

Asthma can be further classified into various subtypes. Neutrophilic asthma, obesity-related asthma, smoking-related asthma and paucigranulocytic asthma are all subtypes of non-Th2 or Th2-low asthma. Neutrophilic asthma is also a subtype of non-allergic asthma and/or severe asthma. Eosinophilic asthma is a subtype of severe asthma, allergic asthma and/or non-allergic asthma.

Eosinophilic asthma is characterised by increased numbers of eosinophils in peripheral blood, lung tissue and airway secretions. Neutrophilic asthma is a severe asthma that may be insensitive to corticosteroid treatment. It is characterised by increased numbers of neutrophils in peripheral blood, lung tissue and airway secretions.

Current treatment for asthma involves a combination of medications, usually administered via inhalers. An individual treatment plan is often drawn up for each patient, depending on their particular needs.

The treatment plan will normally include both quick-relief medications to treat acute symptoms, and long-term control medications to prevent further exacerbation of the condition. There is a requirement for new therapies for the treatment of asthma.

In certain embodiments, the compositions of the invention are for use in treating intermittent asthma, mild persistent asthma, moderate persistent asthma or severe persistent asthma. In certain embodiments, the compositions of the invention are for use in treating severe, moderate, or mild asthma. In certain embodiments, the compositions of the invention are for use in treating Th2-high asthma. In certain embodiments, the compositions of the invention are for use in treating non-Th2 asthma or Th2-low asthma. In some embodiments the compositions of the invention are for use in treating allergic, atopic or extrinsic asthma. Causative allergens can be one or more inhaled allergens, such as pollen, dust mites, pet dander, mould and/or cockroach particles. In some embodiments the compositions of the invention are for use in treating asthma that is not allergic, atopic or extrinsic asthma. In some embodiments the compositions of the invention are for use in treating non allergic, non-atopic or intrinsic asthma. In certain embodiments, the compositions of the invention are for use in treating eosinophilic asthma. In certain embodiments, the compositions of the invention are for use in treating neutrophilic asthma. In certain embodiments, the compositions of the invention are for use in treating asthma which is both eosinophilic and neutrophilic. In certain embodiments, the compositions of the invention are for use in treating asthma that is not eosinophilic asthma. In certain embodiments, the compositions of the invention are for use in treating asthma that is not neutrophilic asthma. In certain embodiments, the compositions of the invention are for use in treating asthma that is neither eosinophilic nor neutrophilic asthma. In certain embodiments, the compositions of the invention are for use in treating obesity-related asthma. In certain embodiments, the compositions of the invention are for use in treating smoking-related asthma. In certain embodiments, the compositions of the invention are for use in treating paucigranulocytic asthma.

Asthma is characterised by specific pathophysiological traits. In some embodiments the compositions of the invention are for use in treating asthma wherein there has been an eosinophilic inflammatory response. In some embodiments the compositions of the invention are for use in treating asthma wherein there has been a neutrophilic inflammatory response. In some embodiments the compositions of the invention are for use in treating asthma wherein there has been infiltration of lymphocytes. In some embodiments the compositions of the invention are for use in treating asthma wherein there has been mast cell activation. In some embodiments the compositions of the invention are for use in treating asthma wherein there has been epithelial cell injury. In some embodiments the compositions of the invention are for use in treating asthma wherein there has been peribronchiolar infiltration. In some embodiments the compositions of the invention are for use in treating asthma wherein there has been perivascular infiltration. In some embodiments the compositions of the invention are for use in treating asthma wherein there has been one or more of these pathophysiological traits, such as two, three, four or more than four of these pathophysiological traits. In certain embodiments, the compositions of the invention result in a reduction of one or more of these pathophysiological traits. In certain embodiments, the compositions of the invention result in a reduction of the eosinophilic and/or neutrophilic inflammatory response. In certain embodiments, the compositions of the invention result in a reduction of peribronchiolar infiltration and/or perivascular infiltration.

Family history of asthma, viral respiratory infections, allergies, smoking, obesity, air pollution, occupational exposure to certain irritants, maternal smoking during pregnancy and premature birth are all considered to be risk factors for asthma. In some embodiments, the compositions of the invention are for use in treating asthma in a subject who has at least one risk factor for asthma. In some embodiments the subject has two risk factors for asthma. In some embodiments the subject has three risk factors for asthma. In some embodiments the subject has four risk factors for asthma. In some embodiments the subject has more than four risk factors for asthma. In some embodiments the subject has a familial history of asthma. In some embodiments the subject has/has had a viral respiratory infection. In some embodiments the subject has/has had allergies. In some embodiments the subject smokes/has smoked. In some embodiments the subject has been obese/is obese. In some embodiments the subject has been exposed to/is being exposed to air pollution. In some embodiments the subject has been exposed to/is being exposed to certain irritants in the work place, such as industrial dusts, wood dusts, chemical fumes, vapours and/or moulds. In some embodiments the mother of the subject smoked during her pregnancy. In some embodiments the subject was born prematurely.

In some embodiments the compositions of the invention are for use in treating asthma resulting from allergens. In some embodiments the compositions of the invention are for use in treating asthma resulting from chronic exposure to nonsteroidal anti-inflammatories, such as aspirin. In some embodiments the compositions of the invention are for use in treating asthma resulting from obesity. In some embodiments the compositions of the invention are for use in treating asthma resulting from chronic exposure to gastrointestinal reflux. In some embodiments the compositions of the invention are for use in treating asthma resulting from pollution. In some embodiments the compositions of the invention are for use in treating asthma resulting from cigarette smoke. In some embodiments the compositions of the invention are for use in treating asthma resulting from rhinitis. In some embodiments the compositions of the invention are for use in treating asthma resulting from stress, anxiety, and/or depression. In some embodiments the compositions of the invention are for use in treating asthma resulting from eosinophil inflammation and/or neutrophil inflammation. In certain embodiments, the patient to be treated has, or has previously been identified as having, elevated neutrophil or eosinophil levels, for example as identified through blood sampling or sputum analysis.

The examples show that treatment with a composition of the invention reduces inflammation in the lung tissue. In some embodiments, the compositions of the invention treat asthma by reducing inflammation in the lung tissue. In some embodiments, the compositions of the invention treat asthma by reducing chronic inflammation and restriction of the airways, such as of the bronchi and bronchioles.

The examples show that treatment with a composition of the invention results in a reduction in the signs of lung inflammation as measured by a qualified histopathologist. In some embodiments, the compositions of the invention treat asthma by reducing neutrophil inflammation. In some embodiments, the compositions of the invention treat asthma by reducing haemorrhage. In some embodiments, the compositions of the invention treat asthma by reducing oedema. In some embodiments, the compositions of the invention treat asthma by reducing necrosis. In some embodiments, the compositions of the invention treat asthma by reducing atelectasis.

The examples demonstrate that the compositions of the invention may be useful for treating asthma and aiding recovery when administered before the injury event occurs. Compositions of the invention for use in treating asthma may be provided to the subject in advance of the onset of asthma, for example in a patient identified as being at risk of asthma. Alternatively, compositions of the invention for use in treating asthma may be provided to the subject whilst they are suffering from asthma. Alternatively, compositions of the invention for use in treating asthma may be provided after asthma has occurred, for example, during recovery.

The compositions of the invention may be useful for preventing the development of asthma in a new-born when administered to the new-born, or to a pregnant woman. The compositions may be useful for preventing the development of asthma in children. The compositions of the invention may be useful for treating adult-onset asthma. The compositions of the invention may be useful for managing or alleviating the symptoms of asthma.

Treatment of asthma may include, for example, effecting an improvement in the disease, an alleviation of the severity of symptoms, a reduction in the damage caused, or a reduction in the frequency of exacerbations or the range of triggers that are a problem for the patient.

In certain embodiments, the compositions of the invention are for use in effecting an improvement in asthma. In certain embodiments, the compositions of the invention are for use in alleviating the severity of symptoms of asthma. In certain embodiments, the compositions of the invention are for use in reducing the damage caused by asthma. In certain embodiments, the compositions of the invention are for use in reducing the frequency of exacerbation of asthma. In certain embodiments, the compositions of the invention are for use in reducing the range of triggers that are a problem for the asthma patient.

As demonstrated in the examples, bacterial compositions of the invention may be effective for treating asthma. In certain embodiments, the composition may be in the form of a bacterial culture. In some embodiments, the composition may preferably be a lyophilisate.

In certain embodiments, the compositions of the invention are for use in combination with a secondary active agent. In certain embodiments, the compositions of the invention are for use in combination with a bronchodilator. In some embodiments, the compositions of the invention are for use in combination with one or more of short acting beta$_2$-adrenoceptor agonists, long acting beta$_2$-adrenoceptor agonists, anticholinergics, corticosteroids, leukotriene inhibitors, mast cell stabilisers, antimuscarinics, xanthines, omalizumab and immune-modulators. The compositions of the invention may improve the patient's response to the secondary active agent.

ARDS

The bacterial compositions of the invention are for use in treating ARDS. The bacterial compositions of the invention are also for use in preventing ARDS.

In preferred embodiments, the compositions of the invention are for use in treating ARDS. In preferred embodiments, the compositions of the invention comprise a strain of the species *Blautia hydrogenotrophica* and are for use in treating ARDS.

As demonstrated in the examples, treatment with compositions of the invention results in a reduction in signs of lung inflammation as measured by a qualified histopathologist, so compositions of the invention may be useful in the treatment of ARDS.

ARDS, also known as acute lung injury (ALI), is a disorder of acute inflammation associated with diffuse alveolar damage (DAD) and disruption of the lung endothelial and epithelial barriers. In the early stages of ARDS, there is an increase in the permeability of the alveolar-capillary barrier, formed of the microvascular endothelium and alveolar epithelium, which leads to an influx of protein-rich fluid into the alveolar space. ARDS is therefore a form of fluid accumulation in the lungs. Any trigger or event which results in damage to the microvascular endothelium and/or the alveolar epithelium could result in ARDS. As well as loss of alveolar-capillary membrane integrity, excessive trans-epithelial neutrophil migration, and release of pro-inflammatory cytokines enhance inflammation and lung damage in ARDS [26]. However, ARDS can develop in the absence of circulating neutrophils, therefore neutrophil independent pathways can also cause ARDS [27].

The symptoms of ARDS often begin within two hours of a triggering event, but can occur after 1-3 days. Signs and symptoms may include shortness of breath, rapid breathing, low oxygen level in the blood due to abnormal ventilation, low blood pressure, confusion and/or extreme tiredness.

The American-European Consensus Conference Committee recommended the adoption of a consensus definition for ALI/ARDS in 1994. The definition relies on the ratio of the partial pressure of oxygen in the patient's arterial blood ($PaO_2$) to the fraction of oxygen in the inspired air ($FiO_2$). This definition requires acute onset, diffuse bilateral pulmonary infiltrates on chest radiograph, a $PaO_2/FiO_2$ ratio of ≤300 mmHg (40 kPa) for ALI and ≤200 mmHg (≤26.7 kPa) for ARDS, and no clinical evidence of left atrial hypertension [28].

However, this international consensus criteria for ARDS was then updated in 2012 and is now known as the "Berlin definition" or "Berlin criteria". The Berlin criteria is a modification of the prior 1994 consensus conference definitions. According to the Berlin criteria, ARDS is characterised by the following:

lung injury of acute onset, within 1 week of an apparent clinical insult and with progression of respiratory symptoms;

radiographic changes (bilateral opacities not fully explained by effusions, consolidation, or atelectasis);

respiratory failure not explained by heart failure or fluid overload;

a decreased $PaO_2/FiO_2$ ratio.

The Berlin criteria discourages the use of the term ALI, instead proposing the sole use of the term ARDS, wherein the ARDS is classified as mild, moderate or severe according to arterial oxygen saturation. Mild ARDS is defined as a $PaO_2/FiO_2$ ratio of 201-300 mmHg (≤39.9 kPa); moderate ARDS is defined as a $PaO_2/FiO_2$ ratio of 101-200 mmHg (≤26.6 kPa); and severe ARDS is defined as a $PaO_2/FiO_2$ ratio of ≤100 mmHg (≤13.3 kPa). The Berlin criteria requires a minimum positive end expiratory pressure (PEEP) of 5 cmH$_2$O for consideration of the $PaO_2/FiO_2$ ratio. The Berlin criteria represent the current international consensus guidelines for both clinical and research classification of ARDS.

Treatment of ARDS is by both ventilation and non-ventilation strategies. To date, the most significant advances in treatment are associated with improved mechanical ventilation. Several studies and clinical trials have shown that a large number of pharmacological strategies are not effective in reducing mortality by ARDS (e.g. surfactant therapy, inhaled nitric oxide, and corticosteroids). There is a requirement for new non-ventilation strategies for the treatment of ARDS.

In some embodiments the compositions of the invention are for use in treating ARDS. In some embodiments the compositions of the invention are for use in treating ARDS as defined by the American-European Consensus Conference Committee. In some embodiments the compositions of the invention are for use in treating ALI as defined by the American-European Consensus Conference Committee. In some embodiments the compositions of the invention are for use in treating ALI wherein the subject has acute onset, diffuse bilateral pulmonary infiltrates on chest radiograph, a $PaO_2/FiO_2$ ratio of ≤300 mmHg (40 kPa) and no clinical evidence of left atrial hypertension. In some embodiments the compositions of the invention are for use in treating ARDS wherein the subject has acute onset, diffuse bilateral pulmonary infiltrates on chest radiograph, a $PaO_2/FiO_2$ ratio of ≤200 mmHg (≤26.7 kPa) and no clinical evidence of left atrial hypertension.

In some embodiments the compositions of the invention are for use in treating ARDS as defined by the Berlin criteria. In some embodiments the compositions of the invention are for use in treating mild, moderate, and/or severe ARDS as defined by the Berlin criteria. In some embodiments the compositions of the invention are for use in treating mild ARDS wherein the subject has a $PaO_2/FiO_2$ ratio of 201-300 mmHg (≤39.9 kPa). In some embodiments the compositions of the invention are for use in treating moderate ARDS wherein the subject has a $PaO_2/FiO_2$ ratio of 101-200 mmHg (≤26.6 kPa). In some embodiments the compositions of the invention are for use in treating severe ARDS wherein the subject has a $PaO_2/FiO_2$ ratio of ≤100 mmHg (≤13.3 kPa).

ARDS is characterised by specific pathophysiological traits [29]. In some embodiments the compositions of the invention are for use in treating ARDS wherein the lung endothelial and epithelial barriers have been disrupted, leading to a loss of alveolar-capillary membrane integrity. In some embodiments the compositions of the invention are for use in treating ARDS wherein there is an increase in the permeability of the alveolar-capillary barrier. In some embodiments the increase in permeability of the alveolar-capillary barrier leads to an influx of fluid into the alveoli. In some embodiments the compositions of the invention are for use in treating ARDS wherein there is DAD, which can be characterised by diffuse inflammation of lung tissue. In some embodiments the compositions of the invention are for use in treating ARDS wherein pro-inflammatory cytokines are released. In some embodiments the compositions of the invention are for use in treating ARDS wherein there is excessive trans-epithelial neutrophil migration. Neutrophils then become activated and release toxic mediators, such as reactive oxygen species and proteases, causing oxidative cell damage and inflammation. In some embodiments the compositions of the invention are for use in treating ARDS wherein there has been one or more of these pathophysiological traits, such as two, three, four or more than four of these pathophysiological traits.

Sepsis, pulmonary infection, pulmonary hypertension, pneumonia, aspiration, trauma, pancreatitis, blood transfusions, burns, near drowning, smoke or toxic gas inhalation, other inhalation injuries and drug overdoses are all considered risk factors for ARDS. The highest incidence of ARDS is associated with severe sepsis and multiple transfusions whereas the lowest incidence is associated with patients with trauma or drug overdoses [30], [31].

In some embodiments, the compositions of the invention are for use in treating ARDS in a subject who has or has had at least one risk factor for ARDS. In some embodiments the subject has or has had two risk factors for ARDS. In some embodiments the subject has or has had three risk factors for ARDS. In some embodiments the subject has or has had four risk factors for ARDS. In some embodiments the subject has or has had more than four risk factors for ARDS. In some embodiments the subject has or has had sepsis. In some embodiments the subject has or has had severe sepsis. In some embodiments the subject has or has had a pulmonary infection. In some embodiments the subject has or has had pulmonary hypertension. In some embodiments the subject has or has had pneumonia. In some embodiments the subject has or has had aspiration. In some embodiments the subject is suffering from or has suffered from trauma. In some embodiments the subject has or has had pancreatitis. In some embodiments the subject has had a blood transfusion. In some embodiments the subject has had multiple blood transfusions, i.e. one or more, two or more, three or more, or four or more blood transfusions. In some embodiments the subject has or has had burns. In some embodiments the subject has suffered from a near drowning incident. In some embodiments the subject has inhaled smoke or toxic gas. In some embodiments the subject has or has had an inhalation injury. In some embodiments the subject has taken a drug overdose.

In some embodiments, the compositions of the invention are for use in treating ARDS resulting from sepsis. In some embodiments, the compositions of the invention are for use in treating ARDS resulting from severe sepsis. In some embodiments, the compositions of the invention are for use in treating ARDS resulting from a pulmonary infection. In some embodiments, the compositions of the invention are for use in treating ARDS resulting from pulmonary hypertension. In some embodiments, the compositions of the invention are for use in treating ARDS resulting from pneumonia. In some embodiments, the compositions of the invention are for use in treating ARDS resulting from aspiration.

In some embodiments, the compositions of the invention are for use in treating ARDS resulting from trauma. In some embodiments, the compositions of the invention are for use in treating ARDS resulting from pancreatitis. In some embodiments, the compositions of the invention are for use in treating ARDS resulting from a blood transfusion. In some embodiments, the compositions of the invention are for use in treating ARDS resulting from multiple blood transfusions, i.e. one or more, two or more, three or more, or four or more blood transfusions. In some embodiments, the compositions of the invention are for use in treating ARDS resulting from burns. In some embodiments, the compositions of the invention are for use in treating ARDS resulting from a near drowning incident. In some embodiments, the compositions of the invention are for use in treating ARDS resulting from inhaled smoke or toxic gas. In some embodiments, the compositions of the invention are for use in treating ARDS resulting from an inhalation injury. In some embodiments, the compositions of the invention are for use in treating ARDS resulting from a drug overdose.

The examples show that treatment with a composition of the invention reduces inflammation in the lung tissue. In some embodiments, the compositions of the invention treat ARDS by reducing inflammation in the lung tissue.

The examples show that treatment with a composition of the invention results in a reduction in the signs of lung inflammation as measured by a qualified histopathologist. In some embodiments, the compositions of the invention treat ARDS by reducing neutrophil inflammation. In some embodiments, the compositions of the invention treat ARDS by reducing haemorrhage. In some embodiments, the compositions of the invention treat ARDS by reducing oedema. In some embodiments, the compositions of the invention treat ARDS by reducing necrosis. In some embodiments, the compositions of the invention treat ARDS by reducing atelectasis.

The examples demonstrate that the compositions of the invention may be useful for treating ARDS and aiding recovery when administered before the injury event occurs. Compositions of the invention for use in treating ARDS may be provided to the subject in advance of the onset of ARDS, for example in a patient identified as being at risk of ARDS. Alternatively, compositions of the invention for use in treating ARDS may be provided to the subject whilst they are suffering from ARDS. Alternatively, compositions of the invention for use in treating ARDS may be provided after ARDS has occurred, for example, during recovery.

The compositions of the invention may be useful for preventing the development of ARDS in a new-born when administered to the new-born, or to a pregnant woman. The compositions may be useful for preventing the development of ARDS in children. The compositions of the invention may be useful for treating adult-onset ARDS. The compositions of the invention may be useful for managing or alleviating the symptoms of ARDS.

Treatment of ARDS may include, for example, effecting an improvement in the disease, an alleviation of the severity of symptoms, a reduction in the damage caused by ARDS, or a reduction in the frequency of exacerbations or the range of triggers that are a problem for the patient.

In certain embodiments, the compositions of the invention are for use in effecting an improvement of ARDS. In certain embodiments, the compositions of the invention are for use in alleviating the severity of symptoms. In certain embodiments, the compositions of the invention are for use in reducing the damage caused by ARDS. In certain embodiments, the compositions of the invention are for use in reducing the frequency of exacerbations or the range of triggers that are a problem for the patient.

As demonstrated in the examples, bacterial compositions of the invention may be effective for treating ARDS. In certain embodiments, the composition may be in the form of a bacterial culture. In some embodiments, the composition may preferably be a lyophilisate.

In certain embodiments, the compositions of the invention are for use in combination with a secondary active agent. In certain embodiments, the compositions of the invention are for use in combination with noninvasive ventilation, mechanical ventilation and conservative fluid management. Other secondary agents include surfactant therapy, inhaled nitric oxide, ketoconazole, simvastatin, ibuprofen, antibiotic therapy and corticosteroids. The compositions of the invention may improve the patient's response to the secondary active agent.

COPD

The bacterial compositions of the invention are for use in treating COPD. The bacterial compositions of the invention are also for use in preventing COPD.

In preferred embodiments, the compositions of the invention are for use in treating COPD. In preferred embodiments, the compositions of the invention comprise a strain of the species *Blautia hydrogenotrophica* and are for use in treating COPD.

As demonstrated in the examples, treatment with compositions of the invention results in a reduction in signs of lung inflammation as measured by a qualified histopathologist, so compositions of the invention may be useful in the treatment of COPD.

COPD is a progressive disease characterised by long-term breathing problems and poor airflow. Symptoms of COPD include shortness of breath, coughing, wheezing, sputum production and/or chest tightness. COPD can be preceded by chronic bronchitis or emphysema. It is typically caused by long-term exposure to irritants, such as tobacco smoke, air pollution or workplace irritants which cause an inflammatory response in the lungs, which in turn results in narrowing of the airways and eventual breakdown of the lung tissue. Genetic predispositions can also be a factor.

Unlike asthma, bronchodilators are not an effective treatment for COPD, providing very little benefit. In fact, there are currently no known treatments for COPD, except lung transplants or lung-volume reduction surgery, which are common only in very young individuals with very severe COPD. Instead, COPD patients are normally offered treatments for their specific symptoms and/or methods to slow progression of the disease. For example, supplemental oxygen, non-invasive ventilation, antibiotics, morphine, pulmonary rehabilitation, flu vaccinations, and in severe cases, corticosteroids can be offered to COPD patients to treat the various symptoms associated with COPD. By far the best method to slow progression of the disease is to reduce or remove patient exposure to the irritant which is identified as the cause. For example, treatments commonly focus on helping a patient to quit smoking, or improving air conditions at their place of work, or at their home. There is a requirement for new therapies for the treatment of COPD.

Family history and long-term exposure to various irritants are considered to be risk factors for COPD. In some embodiments, the compositions of the invention are for use in treating COPD in a subject who has or has had at least one risk factor for COPD. In some embodiments the subject has or has had two risk factors for COPD. In some embodiments the subject has or has had three risk factors for COPD. In some embodiments the subject has or has had four risk factors for COPD. In some embodiments the subject has or has had more than four risk factors for COPD. In some embodiments the subject has a familial history of COPD, emphysema and/or chronic bronchitis. In some embodiments the subject smokes/has smoked. In some embodiments the subject has been exposed to air pollution, such as poorly ventilated cooking fires, in particular those fuelled by coal or biomass fuels, and/or urban air pollution, in particular exhaust gas. In some embodiments the subject has been exposed to certain irritants in the work place, such as one or more of industrial dusts, wood dusts, chemical fumes, chemical vapours and/or moulds, in particular cadmium, isocyanates, silica dust, fiberglass dust and/or fumes from welding.

In some embodiments the compositions of the invention are for use in treating COPD resulting from emphysema. In some embodiments the compositions of the invention are for use in treating COPD resulting from chronic bronchitis. In some embodiments the compositions of the invention are for use in treating COPD resulting from smoking. In some embodiments the compositions of the invention are for use in treating COPD resulting from exposure to air pollutants. In some embodiments the compositions of the invention are for use in treating COPD resulting from exposure to irritants in the work place.

The examples show that treatment with a composition of the invention reduces inflammation in the lung tissue. In some embodiments, the compositions of the invention treat COPD by reducing inflammation in the lung tissue.

The examples show that treatment with a composition of the invention results in a reduction in the signs of lung inflammation as measured by a qualified histopathologist. In some embodiments, the compositions of the invention treat COPD by reducing neutrophil inflammation. In some embodiments, the compositions of the invention treat COPD by reducing haemorrhage. In some embodiments, the compositions of the invention treat COPD by reducing oedema. In some embodiments, the compositions of the invention treat COPD by reducing necrosis. In some embodiments, the compositions of the invention treat COPD by reducing atelectasis.

The examples demonstrate that the compositions of the invention may be useful for treating COPD and aiding recovery when administered before the injury event occurs. Compositions of the invention for use in treating COPD may be provided to the subject in advance of the onset of COPD, for example in a patient identified as being at risk of COPD. Alternatively, compositions of the invention for use in treating COPD may be provided to the subject whilst they are suffering from COPD. Alternatively, compositions of the invention for use in treating COPD may be provided after COPD has occurred, for example, during recovery.

The compositions of the invention may be useful for preventing the development of COPD in a new-born when administered to the new-born, or to a pregnant woman. The compositions may be useful for preventing the development of COPD in children. The compositions of the invention may be useful for treating adult-onset COPD. The compositions of the invention may be useful for managing or alleviating the symptoms of COPD.

Treatment of COPD may include, for example, effecting an improvement in the disease, an alleviation of the severity of symptoms, a reduction in the damage caused, or a reduction in the frequency of exacerbations or the range of triggers that are a problem for the patient.

In certain embodiments, the compositions of the invention are for use in effecting an improvement in COPD. In certain embodiments, the compositions of the invention are for use in alleviating the severity of symptoms of COPD. In certain embodiments, the compositions of the invention are for use in reducing the damage caused by COPD. In certain embodiments, the compositions of the invention are for use in reducing the frequency of exacerbation of COPD. In certain embodiments, the compositions of the invention are for use in reducing the range of triggers that are a problem for the COPD patient.

As demonstrated in the examples, bacterial compositions of the invention may be effective for treating COPD. In certain embodiments, the composition may be in the form of a bacterial culture. In some embodiments, the composition may preferably be a lyophilisate.

In certain embodiments, the compositions of the invention are for use in combination with a secondary active agent. In certain embodiments, the compositions of the invention are for use in combination with one or more of short acting beta$_2$-adrenoceptor agonists, long acting beta$_2$-adrenoceptor agonists, anticholinergics, corticosteroids, leukotriene inhibitors, mast cell stabilisers, antimuscarinics, xanthines, omalizumab and immune-modulators. The compositions of the invention may improve the patient's response to the secondary active agent.

Modes of Administration

Preferably, the compositions of the invention are to be administered to the gastrointestinal tract in order to enable delivery to and/or partial or total colonisation of the intestine with the bacterial strain of the invention. In some embodiments, the term "total colonisation of the intestine" means that bacteria have colonised all parts of the intestine (i.e. the small intestine, large intestine and rectum). In some embodiments, "partial colonisation of the intestine" means that bacteria have colonised some but not all parts of the intestine. In further embodiments of the invention, the term "total colonisation" or "partial colonisation" means that the bacteria are retained permanently or temporarily in the intestine, respectively. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a *theobroma* oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily (either once or several times). The examples demonstrate that administration provides successful colonisation and clinical benefits in treatment of lung injury or lung disease.

In certain embodiments, the compositions of the invention are administered regularly, such as daily, every two days, or weekly, for an extended period of time, such as for at least one week, two weeks, one month, two months, six months, or one year. Administration may not result in permanent colonisation of the intestines, so regular administration for extended periods of time may provide greater therapeutic benefits.

In some embodiments the compositions of the invention are administered for 7 days, 14 days, 16 days, 21 days or 28 days or no more than 7 days, 14 days, 16 days, 21 days or 28 days. For example, in some embodiments the compositions of the invention are administered for 16 days. In some embodiments, the compositions of the invention are administered for 1, 2, 3, 4, 5 or 6 months, over 6 months, or over 1 year.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to treat lung injury or lung disease developing in her child in utero and/or after it is born.

The compositions of the invention may be administered to a patient that has been diagnosed with lung injury or lung disease or a disease or condition associated with lung injury or lung disease, or that has been identified as being at risk of lung injury or lung disease.

The compositions of the invention may be administered to a patient that has been identified as having an abnormal gut microbiota. For example, the patient may have reduced or absent colonisation by *Blautia hydrogenotrophica*.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

In some embodiments, the subject to whom the composition is to be administered is an adult human. In some embodiments, the subject to whom the composition is to be administered is an infant human.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [32-34]. Lyophilisate compositions may be particularly effective. In preferred embodiments, the composition of the invention comprises lyophilised bacteria and is for the treatment of lung injury or lung disease.

Alternatively, the composition of the invention may comprise a live, active bacterial culture. In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonising the intestine. For example, in some embodiments, the bacterial strain in the composition of the invention is viable and capable of partially or totally colonising the intestine.

In some embodiments, the composition comprises a mixture of live bacterial strains and bacterial strains that have been killed.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [35-36].

The composition may be administered orally and may be in the form of a tablet, capsule or powder. Encapsulated products are preferred because *Blautia hydrogenotrophica* are anaerobes.

A composition of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU; in another example from about $1 \times 10^7$ to about $1 \times 10^{11}$ CFU; in another example from about $1 \times 10^8$ to about $1 \times 10^{10}$ CFU; in another example from about $1 \times 10^8$ to about $1 \times 10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1 \times 10^6$ to about $1 \times 10^{11}$ CFU/g, respect to the weight of the composition. For example, the composition may comprise the bacterial strain from about $1 \times 10^3$ to about $1 \times 10^{11}$ CFU/g; for example, from about $1 \times 10^7$ to about $1 \times 10^{10}$ CFU/g; in another example from about $1 \times 10^6$ to about $1 \times 10^{10}$ CFU/g; in another example from about $1 \times 10^7$ to about $1 \times 10^{11}$ CFU/g; in another example from about $1 \times 10^8$ to about $1 \times 10^{10}$ CFU/g; in another example from about $1 \times 10^8$ to about $1 \times 10^{11}$ CFU/g, from about $1 \times 10^8$ to about $1 \times 10^{10}$ CFU/g. The dose may be, for example, 1 g, 3 g, 5 g, or 10 g.

The composition may be formulated as a probiotic. A probiotic is defined by the FAO/WHO as a live microorganism that, when administered in adequate amounts, confers a health benefit on the host.

Typically, a probiotic, such as the composition of the invention, is optionally combined with at least one suitable prebiotic compound. In certain embodiments, the probiotic composition of the present invention includes a prebiotic compound in an amount of from about 1 to about 30% by weight, respect to the total weight composition, (e.g. from 5 to 20% by weight). Known prebiotics include commercial products such as inulin and transgalacto-oligosaccharides.

A prebiotic compound is usually a non-digestible carbohydrate such as an oligo- or polysaccharide, or a sugar alcohol, which is not degraded or absorbed in the upper digestive tract. The carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

Other prebiotic compounds (such as vitamin C, for example), may be included as oxygen scavengers and to improve the delivery and/or partial or total colonisation and survival in vivo. Alternatively, the probiotic composition of the invention may be administered orally as a food or nutritional product, such as milk or whey based fermented dairy product, or as a pharmaceutical product.

The compositions of the invention may comprise pharmaceutically acceptable excipients or carriers. Examples of such suitable excipients may be found in the reference [37]. Acceptable carriers or diluents for therapeutic use are well known in the pharmaceutical art and are described, for example, in reference [38]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid, cysteine and esters of p-hydroxybenzoic acid, for example, in some embodiments the preservative is selected from sodium benzoate, sorbic acid and esters of p-hydroxybenzoic acid. Antioxidants and suspending agents may be also used. A further example of a suitable carrier is saccharose. A further example of a preservative is cysteine.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream, milk-containing food such as sweets.

In some embodiments, the compositions of the invention comprise *Blautia hydrogenotrophica* and do not contain bacteria from any other species, or comprise only de minimis or biologically irrelevant amounts of bacteria from another species. In some embodiments, the compositions of the invention comprise a single strain of *Blautia hydrogenotrophica* and do not contain bacteria from any other strain, or comprise only de minimis or biologically irrelevant amounts of bacteria from another strain.

Such compositions may be a culture that is substantially free from other species of organism. In some embodiments, such compositions may be a lyophilisate that is substantially free from other species of organism.

In some embodiments, the compositions of the invention comprise more than one bacterial strain. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. The invention comprises any combination of the foregoing.

In some embodiments, the composition comprises a microbial consortium. For example, in some embodiments, the composition comprises the *Blautia hydrogenotrophica* bacterial strain as part of a microbial consortium. For example, in some embodiments, the *Blautia hydrogenotrophica* bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a bacterial strain of *Blautia hydrogenotrophica* in combination with a bacterial strain from a different genus. In another example, the composition comprises a bacterial strain of *Blautia hydrogenotrophica* in combination with a bacterial strain from the genus *Blautia* or the composition comprises a bacterial strain of *Blautia hydrogenotrophica* in combination with a bacterial strain from the genus *Blautia* and a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as the *Blautia hydrogenotrophica* strain deposited under accession number DSM 14294, but which is not the *Blautia hydrogenotrophica* strain deposited under accession number DSM 14294, or which is not a *Blautia hydrogenotrophica* or which is not a *Blautia*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human adult faeces. In some embodiments in which the composition of the invention comprises more than one bacterial strain, all of the bacterial strains are obtained from human adult faeces or if other bacterial strains are present they are present only in de minimis amounts. The bacteria may have been cultured subsequent to being obtained from the human adult faeces and being used in a composition of the invention.

In some embodiments, the one or more *Blautia hydrogenotrophica* bacterial strains is/are the only therapeutically active agent(s) in a composition of the invention. In some embodiments, the bacterial strain(s) in the composition is/are the only therapeutically active agent(s) in a composition of the invention.

The compositions for use in accordance with the invention may or may not require marketing approval.

In certain embodiments, the invention provides the above pharmaceutical composition, wherein said bacterial strain is lyophilised. In certain embodiments, the invention provides the above pharmaceutical composition, wherein said bacterial strain is spray dried. In certain embodiments, the invention provides the above pharmaceutical composition, wherein the bacterial strain is lyophilised or spray dried and wherein it is live. In certain embodiments, the invention provides the above pharmaceutical composition, wherein the bacterial strain is lyophilised or spray dried and wherein it is viable. In certain embodiments, the invention provides the above pharmaceutical composition, wherein the bacterial strain is lyophilised or spray dried and wherein it is capable of partially or totally colonising the intestine. In certain embodiments, the invention provides the above pharmaceutical composition, wherein the bacterial strain is lyophilised or spray dried and wherein it is viable and capable of partially or totally colonising the intestine.

In some cases, the lyophilised or spray dried bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is lung injury or lung disease, in particular asthma, ARDS or COPD.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of between 500 mg and 1000 mg, between 600 mg and 900 mg, between 700 mg and 800 mg, between 500 mg and 750 mg or between 750 mg and 1000 mg. In certain embodiments, the invention provides the above pharmaceutical composition, wherein the lyophilised bacteria in the pharmaceutical composition is administered at a dose of between 500 mg and 1000 mg, between 600 mg and 900 mg, between 700 mg and 800 mg, between 500 mg and 750 mg or between 750 mg and 1000 mg.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4° C. or about 25° C. and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap"). The capsule can be a hard or a soft capsule. In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [39]). In some embodiments, the formulation is provided in an intrinsically enteric capsule (for example, Vcaps® from Capsugel).

Culturing Methods

The bacterial strains for use in the present invention can be cultured using standard microbiology techniques as detailed in, for example, references [40-42].

The solid or liquid medium used for culture may for example be YCFA agar or YCFA medium. YCFA medium may include (per 100 ml, approximate values): Casitone (1.0 g), yeast extract (0.25 g), $NaHCO_3$ (0.4 g), cysteine (0.1 g), $K_2HPO_4$ (0.045 g), $KH_2PO_4$ (0.045 g), NaCl (0.09 g), $(NH_4)_2SO_4$ (0.09 g), $MgSO4.7H_2O$ (0.009 g), $CaCl_2$) (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

Bacterial Strains for Use in Vaccine Compositions

The inventors have identified that the bacterial strains of the invention are useful for treating lung disease or lung injury. The bacterial compositions of the invention are also useful in preventing lung disease or lung injury. This may be a result of the effect that the bacterial strains of the invention have on the host immune system. Therefore, the compositions of the invention may also be useful for preventing such diseases or disorders when administered as vaccine compositions. In certain such embodiments, the bacterial strains of the invention are viable. In certain such embodiments, the bacterial strains of the invention are capable of partially or totally colonising the intestine. In certain such embodiments, the bacterial strains of the invention are viable and capable of partially or totally colonising the intestine. In other certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [43-50], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [51]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref [52].

Other possible computer programs are BLAST or FASTA, in which two sequences are aligned for optimal matching of their respective residues (either along the full length of one or both sequences or along a pre-determined portion of one or both sequences). The programs provide a default opening penalty and a default gap penalty, and a scoring matrix such as PAM 250 [53] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences.

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

All patent and literature references cited in the present specification are hereby incorporated by reference in their entirety.

Any reference to a method for treatment comprising administering an agent to a patient, also covers that agent for use in said method for treatment, as well as the use of the agent in said method for treatment, and the use of the agent in the manufacture of a medicament.

The following examples are offered for illustrative purposes only, and are not intended to limit the scope of the present invention in any way.

MODES FOR CARRYING OUT THE INVENTION

Example 1—Effects on Lung Injury or Lung Disease in a Mouse Model

Mice were administered with compositions comprising bacterial strains according to the invention and were subsequently challenged with LPS, a well-established trigger of the inflammatory response. The inflammatory response to LPS in the lungs is a model for lung injury or lung disease. The magnitude of the inflammatory response exhibited by mice treated with compositions of the invention were compared to control groups. The compositions of the invention were found to reduce inflammation of the lung tissue, indicating that they may be useful for treating lung disease or lung injury.

Treatment Schedule

Treatments were administered according to the schedule shown below:

TABLE 1

Treatment Schedule

| Groups | N | Dose | Route | Regimen | Disease Induction | Necropsy |
|---|---|---|---|---|---|---|
| 1 Unchallenged Control | 10 | n/a | n/a | n/a | Day 0: | Day 1 |
| 2 Unchallenged Vehicle (PBS) | 10 | n/a | PO | SID: Day −14-Day 0 | Saline IN | |
| 3 Vehicle (PBS) | 10 | n/a | PO | SID: Day −14-Day 0 | Day 0: | |
| 4 Methylprednisolone | 10 | 30 mg/kg | PO IV | SID: Day −14-Day 0 (veh, WFI) −0.5 hrs, 6 hrs and 12 hrs post-UPS (methylprednisolone) | LPS IN | |
| 5 Blautix FDP | 10 | 2 × 10^8 | PO | SID: Day −14-Day 0 | | |
| 6 Lyobuffer FDP | 10 | n/a | PO | SID: Day −14-Day 0 | | |

The administration volume was 100 µl per mouse,
n/a: not applicable,
SID: once per day,
PO: oral administration (gavage),
LPS: lipopolysaccharides,
IN: intra-nasal,
IV: intravenous,
WFI: water for injection When handling the animals, gloves were changed between each treatment group and sprayed with 70% ethanol solution between each cage of the same group to minimise any risk of contamination. All treatments were administered at random and alternated daily so as to prevent the same groups being treated at the same time each day.

Adult female C57BL/6 mice were randomized according to their bodyweights into six experimental groups (Groups 1, 2, 3, 4, 5 and 6; ten mice per group), and allowed to acclimatize for one week. The first dosing day was Day −14 (pre-treatment baseline). Groups 2-6 were administered treatments daily, as outlined in Table 1, at random, and alternated daily so as to prevent the same groups being treated at the same time each day. On Day 0, Groups 3-6 received lipopolysaccharides (LPS, Sigma) in saline (NaCl 0.9%) administered by intra-nasal route; Groups 1 and 2 received only saline (NaCl 0.9%) administered by intra-nasal route. Intra-nasal administrations were performed under isoflurane anaesthesia. Mice were then scored for clinical signs of acute lung injury six, twelve and twenty-four hours after LPS administration.

Lung Dissection

For Groups 1-6, on Day 1, lungs were dissected out, transferred into tissue fixative then embedded in paraffin wax and stored until histopathology analysis.

Caecum Dissection

For Groups 1-6, on Day 1, the full caecum (and its contents) and two centimetres of each of the following sections were stored in Qiagen pre-filled tubes (5 ml) overnight at 4° C. then stored at −80° C.: duodenum, jejunum, ileum upstream of caecum, ascending colon, transverse colon and descending colon.

Body Weights

For Groups 1-6, from Day −14, animals were weighed three times per week until Day 1. All animals were also weighed on Day 0 and Day 1. Animal manipulation and handling was carried out at random, alternating each day, so as to prevent, the same animals being handled at the same time points.

Faecal Pellets

For Groups 1-6, faecal pellets were collected from each animal on Day −14 and Day −2, and immediately snap-frozen and stored at −80° C.

Blood Sampling

For Groups 1-6, on Day −14 and 1, blood samples were collected from a caudal (tail) vein of each animal, half the volume into EDTA and half the volume into lithium-heparin tubes. Tubes were centrifuged for 10 min at 2000 g+4° C., and plasma was pipetted out and placed into 2 aliquots. On Day 1, terminal blood samples were collected from the orbital sinus and collected in EDTA tubes and also processed to isolate plasma. Groups were randomised when taking samples at each time point. Samples were stored at −80° C.

Strain

*Blautia hydrogenotrophica* bacterium deposited under accession number DSM 14294. Provided as a freeze-dried powder and reconstituted.

Readouts

Clinical Observations

For Groups 1-6, on Day 0, at T=0 hours, 6 hours, 12 hours and on Day 1 at T=24 hours, animals were scored for clinical signs to include abnormal posture (hunched), abnormal coat condition (piloerection) and abnormal activity levels (reduced or increased activity).

Lung Histopathology

For Groups 1-6, lung sections were prepared, stained with Haematoxylin and Eosin then scored for signs of inflammation by a qualified histopathologist. Two standard sections were taken from each set of lungs: from one cranial lobe and the contralateral caudal lobe. The scoring system was adapted from Su et al [54]. The most severely affected lung section was scored. Neutrophil inflammation, haemorrhage, oedema, necrosis and atelectasis were each scored on the scale shown below:

(0) Normal;
(1) 0-25% of area affected;
(2) 25-50% of area affected;
(3) 50-75% of area affected;
(4) 75-100% of area affected.

Results

Bodyweights in grams are shown in FIG. 1. Variation in bodyweight observed on Day 1 in FIG. 1 was as expected for this model. Data are presented as mean±SEM.

Figure 2:
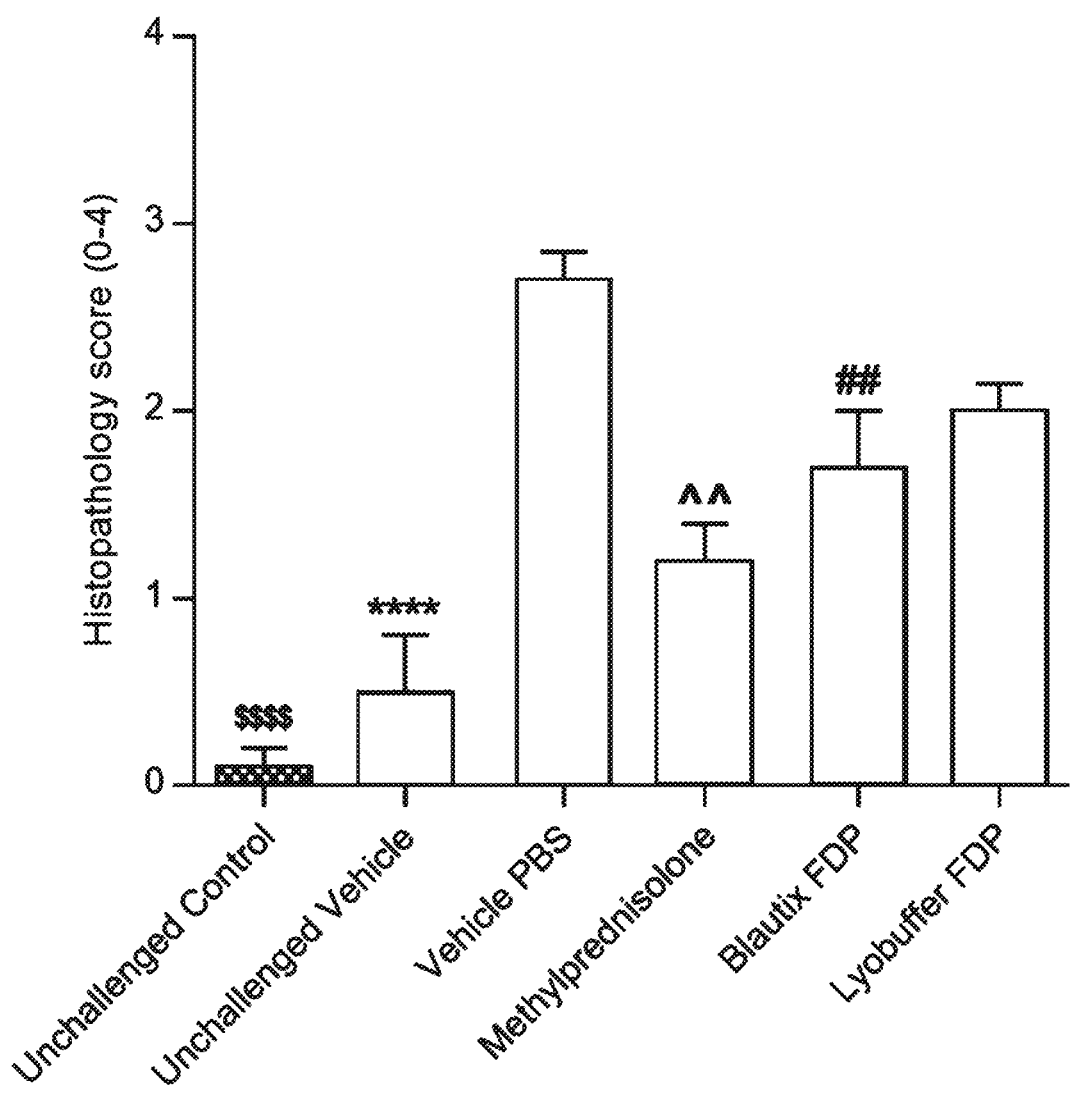
FIG. 2: Histopathology scoring analysis of Groups 1-6. Neutrophil inflammation, haemorrhage, oedema, necrosis and atelectasis of lung sections were each scored on a scale of 0-4. Average total histopathological scores are shown for each of Groups 1-6. $$$ and ****: p<0.0001 vs. vehicle group. ^^ and ##: p<0.01 vs. vehicle group.
Figure 3F:
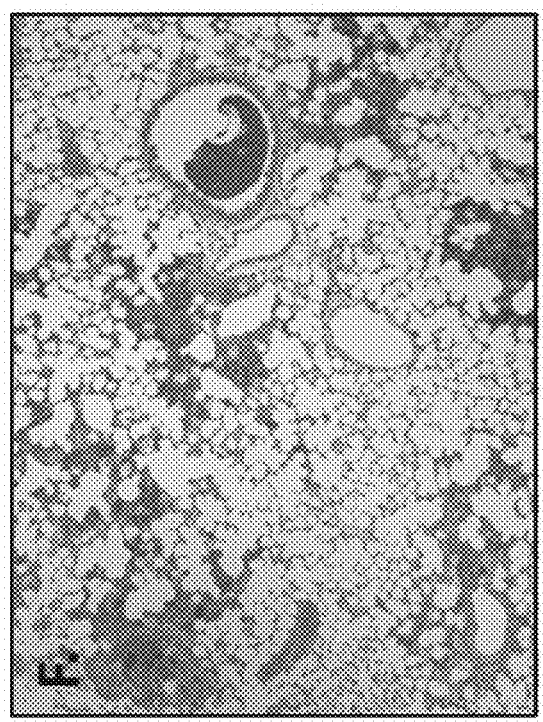
Figure 3H:
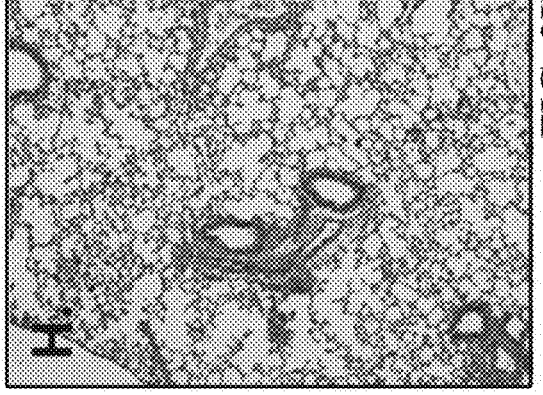
Figure 3E:
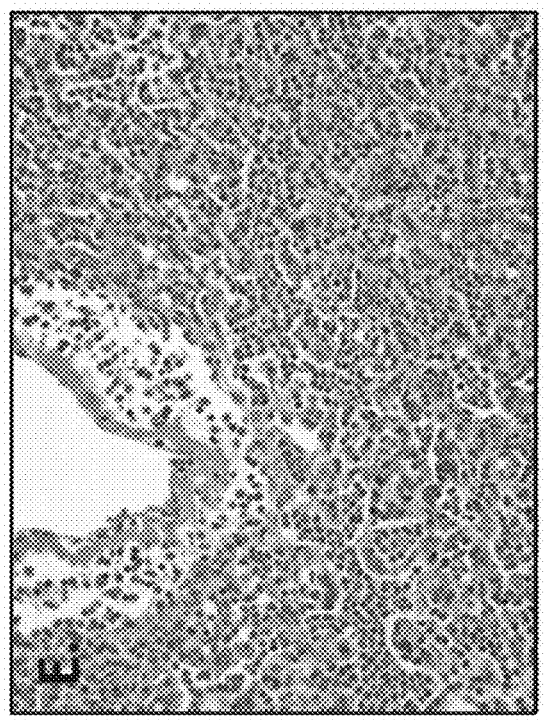
Figure 3G:
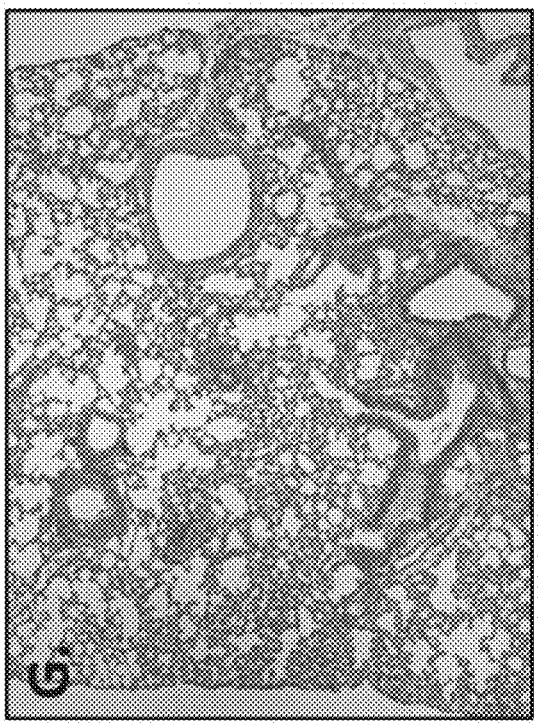

Overall, in LPS challenged animals, the histopathological changes affected the cranial lobe more severely than the caudal lobe in most cases, as expected in this model. These changes include neutrophilic inflammation with a peribronchiolar, perivascular, interstitial and intra-alveolar distribution; focal intra-alveolar or perivascular haemorrhage and focal atelectasis and emphysema. There was none to negligible pathology in the lungs of Groups 1 and 2 as expected in unchallenged animals. The difference between these groups and the vehicle groups was significant ($p<0.0001$), as assessed by One-way ANOVA followed by Dunnett's post-test. The remaining groups all showed pathological change of varying degrees; this was most severe in Group 3 and of lesser severity in the Methylprednisolone (Group 4), Blautix FDP (Group 5) and Lyobuffer FDP (Group 6) groups (FIG. 2). Histopathology scoring was significantly improved in the Methylprednisolone ($p<0.01$) and Blautix FDP ($p<0.01$) groups, as assessed by One-way ANOVA followed by Dunnett's post-test and unpaired two-tailed Student's t-test, respectively. Methylprednisolone and Blautix FDP significantly reduced histopathology scores compared to vehicle. See FIG. 3 for representative histopathology images.

Example 2—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Sequences

```
(Blautia hydrogenotrophica strain S5a36 16S ribosomal RNA gene,
partial sequence - X95624.1)
                                                           SEQ ID NO: 1
   1 gatgaacgct ggcggcgtgc ttaacacatg caagtcgaac gaagcgatag agaacggaga 61 tttcggttga agttttctat tgactgagtg gcggacgggt gagtaacgcg tgggtaacct 121 gccctataca gggggataac agttagaaat gactgctaat accgcataag cgcacagctt 181 cgcatgaagc ggtgtgaaaa actgaggtgg tataggatgg acccgcgttg gattagctag 241 ttggtgaggt aacggcccac caaggcgacg atccatagcc ggcctgagag ggtgaacggc 301 cacattggga ctgagacacg gcccaaactc ctacgggagg cagcagtggg gaatattgca 361 caatgggggaa aaccctgatg cagcgacgcc gcgtgaagga agaagtatct cggtatgtaa 421 acttctatca gcagggaaga aagtgacggt acctgactaa gaagccccgg ctaattacgt 481 gccagcagcc gcggtaatac gtaaggggca agcgttatcc ggatttactg ggtgtaaagg 541 gagcgtagac ggtttggcaa gtctgatgtg aaaggcatgg gctcaacctg tggactgcat 601 tggaaactgt cagacttgag tgccggagag gcaagcggaa ttcctagtgt agcggtgaaa 661 tgcgtagata ttaggaggaa caccagtggc gaaggcggcc tgctggacgg taactgacgt 721 tgaggctcga aagcgtgggg agcaaacagg attagatacc ctggtagtcc acgctgtaaa 781 cgatgaatac taggtgtcgg gtggcaaagc cattcggtgc cgcagcaaac gcaataagta 841 ttcccacctg gggagtacgt tcgcaagaat gaaactcaaa ggaattgacg gggacccgca 901 caagcggtgg agcatgtggt ttaattcgaa gcaacgcgaa gaaccttacc aaatcttgac 961 atccctctga ccgggaagta atgttccctt ttcttcggaa cagaggagac aggtggtgca 1021 tggttgtcgt cagctcgtgt cgtgagatgt tgggttaagt cccgcaacga gcgcaaccct 1081 tattcttagt agccagcagg tagagctggg cactctaggg agactgccag ggataacctg 1141 gaggaaggtg gggatgacgt caaatcatca tgccccttat gatttgggct acacacgtgc
```

```
1201 tacaatggcg taaacaaagg gaagcgaagg ggtgacctgg agcaaatctc aaaaataacg 1261 tctcagttcg gattgtagtc tgcaactcga ctacatgaag ctggaatcgc tagtaatcgc 1321 gaatcagaat gtcgcggtga atacgttccc gggtcttgta cacaccgccc gtcacaccat 1381 gggagtcagt aacgcccgaa gtcagtgacc caaccnaaag gagggagctg ccgaaggtgg 1441 gactgataac tggggtga
```

REFERENCES

[1] Spor et al. (2011) *Nat Rev Microbiol.* 9(4):279-90.
[2] Eckburg et al. (2005) *Science.* 10; 308(5728):1635-8.
[3] Tap et al. (2009) *Environ Microbiol,* 11(10):2574-84
[4] Macpherson et al. (2001) *Microbes Infect.* 3(12):1021-35
[5] Macpherson et al. (2002) *Cell Mol Life Sci.* 59(12):2088-96.
[6] Mazmanian et al. (2005) *Cell* 15; 122(1):107-18.
[7] Frank et al. (2007) *PNAS* 104(34):13780-5.
[8] Scanlan et al. (2006) *J Clin Microbiol.* 44(11):3980-8.
[9] Kang et al. (2010) *Inflamm Bowel Dis.* 16(12):2034-42.
[10] Machiels et al. (2013) *Gut.* 63(8):1275-83.
[11] Lopetuso et al. (2013), *Gut Pathogens,* 5: 23
[12] WO 2013/050792
[13] WO 03/046580
[14] WO 2013/008039
[15] WO 2014/167338
[16] Lee and Lee (2014) *World J GastroenteroL* 20(27): 8886-8897.
[17] WO 2017/148596
[18] WO 2018/011593
[19] WO 2018/011594
[20] WO 01/85187
[21] WO 2016/203218
[22] Liu et al. (2008) *Int J Syst Evol Microbiol* 58, 1896-1902.
[23] Bernalier et al. (1996) *Arch. Microbial.* 166 (3), 176-183.
[24] Masco et al. (2003) *Systematic and Applied Microbiology,* 26:557-563.
[25] Srůtková et al. (2011)*J. Microbiol. Methods,* 87(1):10-6.
[26] Ware and Matthay (2000) *N Engl J Med.* 342:1334-1349.
[27] Martin et al. (1989) *J Clin Invest.* 84:1609-1619.
[28] Bernard et al. (1994) *J Crit Care.* 9:72-81.
[29] Pierrakos et al. (2012)*J Clin Med Res.* 4(1): 7-16.
[30] Rubenfeld et al. (2005) *N Engl J Med.* 353:1685-1693.
[31] Hudson and Steinberg (1999) *Chest.* 116:74S-82S.
[32] Miyamoto-Shinohara et al. (2008) *J. Gen. Appl. Microbiol.,* 54, 9-24.
[33] Cryopreservation and Freeze-Drying Protocols, ed. by Day and McLellan, Humana Press.
[34] Leslie et al. (1995) *Appl. Environ. Microbiol.* 61, 3592-3597.
[35] Mitropoulou et al. (2013) *J Nutr Metab.* (2013) 716861.
[36] Kailasapathy et al. (2002) *Curr Issues Intest Microbiol.* 3(2):39-48.
[37] Handbook of Pharmaceutical Excipients, 2nd Edition, (1994), Edited by A Wade and PJ Weller
[38] Remington's Pharmaceutical Sciences, Mack Publishing Co. (A. R. Gennaro edit. 1985)
[39] US 2016/0067188
[40] *Handbook of Microbiological Media, Fourth Edition* (2010) Ronald Atlas, CRC Press.
[41] *Maintaining Cultures for Biotechnology and Industry* (1996) Jennie C. Hunter-Cevera, Academic Press
[42] Strobel (2009) *Methods Mol Biol.* 581:247-61.
[43] Gennaro (2000) *Remington: The Science and Practice of Pharmacy.* 20th edition, ISBN: 0683306472.
[44] *Molecular Biology Techniques: An Intensive Laboratory Course,* (Ream et al., eds., 1998, Academic Press).
[45] *Methods In Enzymology* (S. Colowick and N. Kaplan, eds., Academic Press, Inc.)
[46] *Handbook of Experimental Immunology,* Vols. I-IV (D. M. Weir and C. C. Blackwell, eds, 1986, Blackwell Scientific Publications)
[47] Sambrook et al. (2001) *Molecular Cloning: A Laboratory Manual,* 3rd edition (Cold Spring Harbor Laboratory Press).
[48] *Handbook of Surface and Colloidal Chemistry* (Birdi, K. S. ed., CRC Press, 1997)
[49] Ausubel et al. (eds) (2002) *Short protocols in molecular biology,* 5th edition (Current Protocols).
[50] *PCR (Introduction to Biotechniques Series),* 2nd ed. (Newton & Graham eds., 1997, Springer Verlag)
[51] *Current Protocols in Molecular Biology* (F. M. Ausubel et al., eds., 1987) Supplement 30
[52] Smith & Waterman (1981) *Adv. Appl. Math.* 2: 482-489.
[53] Dayhoff et al. (1978) *Atlas of Protein Sequence and Structure,* vol. 5, supp. 3
[54] Su et al. (2004) *Intensive Care Medicine* 30, 133-140.

The invention claimed is:

1. A method of treating lung injury or lung disease in a subject in need thereof, comprising administering to the subject a pharmaceutical composition comprising a lyophilized bacterial strain of the genus *Blautia*, wherein the lyophilized bacterial strain comprises a polynucleotide sequence of a 16S rRNA gene that has at least 95% sequence identity to the polynucleotide sequence of SEQ ID NO:1, and a pharmaceutically acceptable excipient, diluent, or carrier,
wherein the lung injury or the lung disease is non-asthma lung injury or non-asthma lung disease.

2. The method of claim 1, wherein the lung injury or the lung disease is mediated by inflammation in a lung tissue of the subject.

3. The method of claim 2, wherein the pharmaceutical composition reduces inflammation in the lung tissue.

4. The method of claim 2, wherein the lung injury or the lung disease comprises bronchiectasis, bronchiolitis, bronchitis, chronic cough, cystic fibrosis, emphysema, human metapneumovirus (h1VIPV) infection, influenza, pertussis, pleural cavity diseases, pneumonia, respiratory syncytial virus (RSV), sarcoidosis, severe acute respiratory syndrome (SARS), tuberculosis, or upper respiratory tract infections.

5. The method of claim 1, wherein the lung injury or the lung disease comprises acute respiratory distress syndrome (ARDS) or chronic obstructive pulmonary disease (COPD).

6. The method of claim 1, wherein the administering the pharmaceutical composition reduces one or more of neutrophil inflammation, haemorrhage, oedema, necrosis, and atelectasis in the lung tissue.

7. The method of claim 6, wherein the administering the pharmaceutical composition reduces all of neutrophil inflammation, haemorrhage, oedema, necrosis, and atelectasis in the lung tissue.

8. The method of claim 1, wherein the bacterial strain has a 16s rRNA gene sequence that has at least 98% sequence identity to the polynucleotide sequence of SEQ ID NO:1, as determined by a Smith-Waterman homology search algorithm using an affine gap search with a gap open penalty of 12 and a gap extension penalty of 2.

9. The method of claim 1, wherein the bacterial strain has a 16s rRNA gene sequence comprising the polynucleotide sequence of SEQ ID NO:1.

10. The method of claim 1, wherein the pharmaceutical composition comprises a single strain of the genus *Blautia*.

11. The method of claim 1, wherein the pharmaceutical composition comprises the bacterial strain of the genus *Blautia* as a part of a microbial consortium.

12. The method of claim 1, wherein the bacterial strain is of the species *Blautia hydrogenotrophica*.

13. The method of claim 12, wherein the bacterial strain is the strain deposited as accession number DSM 14294 at the Deutsche Sammlung von Mikroorganismen (German Microorganism Collection), a biotype thereof, or a derivative thereof.

14. The method of claim 1, wherein the pharmaceutical composition is formulated for oral delivery.

15. The method of claim 1, wherein the bacterial strain is viable.

16. The method of claim 1, wherein the bacterial strain is capable of colonizing the intestine.

17. The method of claim 1, wherein the 95% sequence identity is determined by a Smith-Waterman homology search algorithm using an affine gap search with a gap open penalty of 12 and a gap extension penalty of 2.

18. A method of reducing damage in a lung tissue caused by lung injury or lung disease in a subject in need thereof, comprising administering to the subject a pharmaceutical composition comprising a lyophilized bacterial strain of the genus *Blautia*, wherein the lyophilized bacterial strain comprises a polynucleotide sequence of a 16S rRNA gene that has at least 95% sequence identity to the polynucleotide sequence of SEQ ID NO:1, and a pharmaceutically acceptable excipient, diluent, or carrier, wherein the lung injury or the lung disease is non-asthma lung injury or non-asthma lung disease.

19. The method of claim 18, wherein the lung injury or the lung disease comprises acute respiratory distress syndrome (ARDS) or chronic obstructive pulmonary disease (COPD).

20. The method of claim 4, wherein the influenza is pandemic flu and the pleural cavity disease is pleurisy.

* * * * *